United States Patent [19]

Millar et al.

[11] Patent Number: 4,985,584

[45] Date of Patent: * Jan. 15, 1991

[54] PROCESS FOR THE PRODUCTION OF HIGH ENERGY MATERIALS

[75] Inventors: Ross W. Millar; Norman C. Paul, both of Hertfordshire; David H. Richards, Essex, all of England

[73] Assignee: Secretary of State for Defence, London, England

[*] Notice: The portion of the term of this patent subsequent to Apr. 11, 2006 has been disclaimed.

[21] Appl. No.: 923,054

[22] Filed: Oct. 27, 1986

Related U.S. Application Data

[63] Continuation-in-part of Ser. No. 887,990, Jun. 27, 1986, abandoned, which is a continuation-in-part of Ser. No. 794,340, Nov. 5, 1985, Pat. No. 4,820,859, which is a continuation of Ser. No. 507,170, Jun. 27, 1983, abandoned.

[30] Foreign Application Priority Data

| Jul. 15, 1982 | [GB] | United Kingdom | 8220082 |
| Oct. 25, 1985 | [GB] | United Kingdom | 8526387 |
| Nov. 26, 1985 | [GB] | United Kingdom | 8529094 |

[51] Int. Cl.$^5$ .................................................. C07C 77/02
[52] U.S. Cl. .................................. 558/483; 525/333.2; 525/377; 558/484; 558/485; 558/487; 558/480
[58] Field of Search ............... 558/480, 484, 483, 487, 558/485; 525/377, 333.2

[56] References Cited

U.S. PATENT DOCUMENTS

| 3,058,994 | 10/1962 | Schrage | 549/510 |
| 3,549,687 | 12/1970 | Bachman et al. | 558/480 |
| 3,631,110 | 12/1971 | Smetana | 558/480 |
| 3,721,698 | 3/1973 | Stogryn et al. | 558/487 |
| 4,820,859 | 4/1989 | Miller et al. | 558/483 |

FOREIGN PATENT DOCUMENTS

899993  6/1962  United Kingdom .

OTHER PUBLICATIONS

English Translation of French Patent 1,000,372 of Boileau.
Kirk-Othmer, Encyclopedia of Chemical Technology, 3rd Edition, vol. 9, pp. 572-585.
Chemical Abstracts, vol. 84, No. 15, Apr. 12, 1876.

*Primary Examiner*—Edward A. Miller
*Attorney, Agent, or Firm*—Cushman, Darby & Cushman

[57] ABSTRACT

A process for the production of a high energy nitrate ester involves reacting, in an inert organic solvent, a heterocyclic compound, selected from oxiranes, oxetanes, N-substituted aziridines and N-substituted azetidines, with either $N_2O_4$ or $N_2O_5$, and when the compound is reacted with $N_2O_4$, oxidizing the O- or N-nitrate substituents or substituent in the product to O- or N-nitrate substituent or substituents. The remaining ring carbon atoms on the heterocyclic compound may be substituted or unsubstituted. Preferred substituent groups for the C and/or N ring atoms on the compound include alkyl, cyanoalkyl, haloalkyl, nitroalkyl, and substituted aryl.

Several novel nitrate ester are also provided, including nitrated derivatives of polybutadiene, in which between 1% and 25% of the carbon atoms in the polymer are substituted by vicinal nitrate ester ($-ONO_2$) groups.

25 Claims, No Drawings

PROCESS FOR THE PRODUCTION OF HIGH ENERGY MATERIALS

The present application is a continuation-in-part of application Ser. No. 887,990 filed June 27, 1986, now abandoned, which is a continuation-in-part of application Ser. No. 794,340 filed Nov. 5, 1985 which issued on Apr. 11, 1989 as U.S. Pat. No. 4,820,859, which is a file-wrapper-continuation of application Ser. No. 507,170 filed June 27, 1983, now abandoned.

This invention relates to a process for the production of high energy materials containing nitrate ester (—$ONO_2$) groups, to high energy materials produced thereby and to certain novel high energy materials.

By definition such high energy materials can be either pure single substances or a mixture of substances which are capable of liberating energy, in the absence of free oxygen, sufficiently rapidly to cause sudden changes in temperature and pressure in their immediate vicinity. These materials are used as explosives and solid rocket propellants, often in admixture with other ingredients, and usually have a high usuable oxygen content, normally referred to as the oxygen balance. This oxygen enables rapid exothemic chemical reactions in the materials to occur once initiated, usually with the liberation of large quantities of gases such as $NO_x$, $CO$, $CO_2$ and $H_2O$, which gases provides the source of the pressure change.

At present the manufacture of the group of high energy materials which contain nitrate ester (—$ONO_2$) substituents or the analogous materials which contain a mixture of nitrate ester substituents generally requires the use of strong mineral acids (especially $HNO_3$/$H_2SO_4$ mixtures). For example, the manufacture of aliphatic nitrate esters such as ethylene glycol dinitrate and nitroglycerine, both widely used high energy materials, requires the mixed acid nitration of polyhydric alcohols which correspond to these esters. These conditions present the manufacturer of these materials with a number of problems which he must overcome if the method of production is to meet modern standards of safety. These problems include the control, containment and disposal of a highly dangerous and corrosive reaction mixture (strong mineral acids).

One method which goes some way to relieve the problems associated with the use of strong mineral acids is given in French Pat. No. 1,100,372 (Boileau), which describes the reaction of ethylene oxide with nitrogen tetroxide either in the vapour phase or within an inert organic solvent to produce a mixture of nitrated monomers, dimers and polymers. The principal product of the ring-opening reaction described by Boileau, a vicinal nitrite-nitrate ester of formula $CH_2(ONO_2)CH_2(ONO)$ is however hydrolytically unstable and so is not suitable for use as an explosive. Boileau further describes the recovery of hydrolytically stabilised, but relatively low energy, mononitrates from the products of these reactions by a hydrolysis reaction in which the nitrite-nitrate products are treated with an alcohol under reflux for 1 hour and are then distilled to drive off volatile matter. The hydrolysis reaction which involves the principal vicinal nitrite-nitrate product may be represented by the following equation:

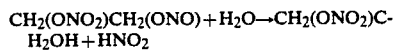

$CH_2(ONO_2)CH_2(ONO) + H_2O \rightarrow CH_2(ONO_2)CH_2OH + HNO_2$

The method of Boileau therefore falls short of providing an alternative route to inherently higher energy nitrate esters, such as nitroglycerine and ethylene glycol dinitrate, which are more hydrolytically stable than the aforementioned vicinal nitrite-nitrate and which contain a high density of nitrate ester groups per molecule. Other disadvantages of Boileau's method include that mineral acid ($HNO_2$) contaminant is still liberated in appreciable amounts during one of the process steps disclosed, and the principal product is generally contaminated with significant amounts of nitrated di- and polyethers. The method is, furthermore, wasteful of nitrogen oxide because in the overall reaction to produce a hydrolytically-stabilised hydroxy-nitrate product, only one nitrate ester group is generated per molecule of final hydrolysed product for each molecule of dinitrogen tetroxide consumed.

It is one object of the present invention to overcome at least some of the problems outlined above by providing a process of preparing a high energy material free of nitrite ester groups, which does not require the disposal of large quantities of mineral acid and which utilises a nitrating agent more efficiently than the method described in French Pat. No. 1,100,372.

According to a first aspect of the present invention, there is provided a process for the production of a high energy material which comprises reacting a heterocylic strained ring compound with a nitrogen oxide selected from the group dinitrogen tetroxide ($N_2O_4$) and dinitrogen pentoxide ($N_2O_5$) to afford a ring-opened product and, when the nitrogen oxide is dinitrogen tetroxide, oxidising X-nitroso (XNO) substituents or substituent produced by the reaction with dinitrogen tetroxide to X-nitro ($XNO_2$) substituents or substituent, wherein X is an atom selected from Group VIb and Group Vb of the Periodic Table.

In this specification, the term heterocyclic strained ring compound means a carbon-based (usually organic) optionally-substituted heterocyclic compound containing 3 or 4 atoms per ring and up to 2 ring heteroatoms X, selected from Group Vb and Group VIb of the Periodic Table, which may be the same or different. X is preferably selected from oxygen and nitrogen. Examples of strained ring compounds containing two heteroatoms X per ring are 1-azirines, diaziridines, oxaziridines and dioxetanes. More preferably, however, the strained ring compound is based on a saturated alicyclic nucleus containing only one heteroatom X. Most preferably, the heterocyclic strained ring compound is selected from the group consisting of oxiranes, oxetanes, aziridines and azetidines in which case when the nitrogen oxide employed in the present process is $N_2O_4$, the monovalent nitrite ester (—ONO) or divalent N-nitroso (>NNO) substituent or substituents produced by the reaction with $N_2O_4$ is or are oxidised to monovalent nitrate ester (—$ONO_2$) or divalent N-nitro (>$NNO_2$) substituent or substituents. The thio analogues of oxiranes and oxetanes (thiiranes and thietanes) may also be used in the present process although these are less preferred.

The overall ring-opening reaction which is believed to occur when compounds from the group oxiranes, oxetanes, N-substituted aziridines and N-substituted azetidines are reacted in accordance with the process of the present invention may be summarised by the following equations, although the invention is not limited in any way by this explanation:

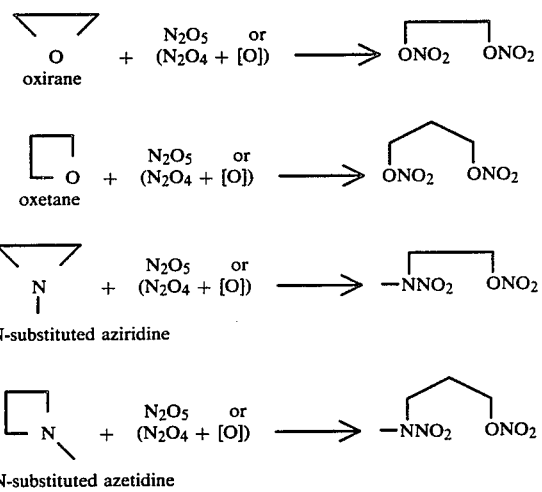

It may be seen from these overall reaction equations that in theory the principal products of these reactions take up 100% of the nitrogen oxide consumed in the reaction, without any nitrated by-product being generated. This represents a highly efficient utilisation of available nitrogen oxide. The overall reaction with aziridines and azetidines which are not N-substituted is less clear because a mixture of nitrate ester products are generally produced when these strained ring compounds are used in the present process.

In this specification, the term heterocyclic strained ring compound, which is preferably selected from the groups oxiranes, oxetanes, aziridines and azetidines, encompasses both the unsubstituted compound and the substituted derivatives of the compound. In the latter case the heterocyclic strained ring may be substituted by any substituent group and at an one or more available ring position. Preferably not more than two of the available carbon atoms on the heterocyclic ring are substituted.

At least one of the carbon atoms on the heterocyclic strained ring nucleus, especially the nucleus of oxirane, oxetane, aziridine or azetidine, is preferably substituted by at least one of the following groups: halo (especially chloro), nitro, cyano, hydroxy, azido, primary amino, and carbon-compatible organic radical.

The carbon compatible organic radical may be an optionally-substituted aliphatic, aromatic or alicyclic radical. Aromatic radicals are preferably from the benzene and the monocyclic heteroaromatic series, and examples include phenyl, phenylene, pyridyl, and pyrimidyl. Aliphatic radicals are preferably from the alkyl, alkoxyl, alkenyl, acyl, aldehydo, keto, secondary or tertiary amino, amido (carbamyl), carboxylate ester, carboxylic acid, ether and alkynyl series containing up to 10, more preferably up to 5, carbon atoms, and examples include $C_1-C_5$ alkyl, ethenyl (vinyl), acetoxy, and acetyl. Alicyclic radicals are preferably either homocyclic containing from 4–8 carbon atoms, such as cyclohexyl, or heterocyclic containing 3 to 8 ring atoms, especially 3 or 4 ring atoms, such as oxiranyl, oxetanyl, aziridinyl or azetidenyl, provided that aziridinyl and azetidinyl radicals are either N-substituted or are attached through their N-ring atoms to the heterocyclic strained ring nucleus. The carbon-compatible organic radical may be monovalent and attached to a single peripheral carbon atom on the strained ring heterocyclic nucleus, or it may be polyvalent, preferably divalent, and attached to the same or adjacent carbon atoms on the strained ring nucleus. For example, two adjacent carbon atoms on the strained ring nucleus may be joined by a divalent organic radical comprising a straight chain alkane bridging group, especially a tetramethylene bridging group. Where the radical is polyvalent it may be attached to two or more heterocyclic strained ring nuclei. In particular, the strained ring nucleus may be disubstituted with a divalent organic radical as in, for example, an epoxidised polymer such as epoxidised polybutadiene.

Examples of substituents for the aromatic radicals are alkyl, alkenyl, alkoxyl, alkylthio, and halo (especially chloro), nitro, azido and and cyano substituted derivatives thereof, aryl, especially phenyl, azido, hydroxy, carboxy, amino, halo, nitro, cyano, and optionally-substituted oxiranyl, oxetanyl, aziridinyl and azetidinyl provided that aziridinyl and azetidinyl substituents are either N-substituted or are attached to the aromatic radical through their N ring atoms. Examples of substituents for the aliphatic and alicyclic radicals are alkoxy, halo, cyano, nitro, hydroxy, azido, divalent oxy substituting adjacent carbon atoms on the radicals, aryl, amino and optionally-substituted oxiranyl, oxetanyl, aziridinyl and azetidinyl provided that aziridinyl and azetidinyl substituents are either N-substituted or are attached to the aliphatic or alicyclic radical through their N-atoms. In these substituents the alkyl and alkenyl groups preferably contain up to 10, and more preferably up to 5, carbon atoms, the aryl groups are preferably homo-or heteromonocyclic, and the oxiranyl, oxetanyl, aziridinyl and azetidinyl groups are, when substituted, preferably substituted by at least one group selected from hydroxy, halo, cyano, nitro, or $C_1-C_5$ alkyl optionally substituted with cyano, nitro, halo or hydroxy. Oxiranyl, oxetanyl, aziridinyl and azetidinyl are defined in this specification by the following monovalent unsubstituted structures which may be attached to the substituted molecule at any available ring position:

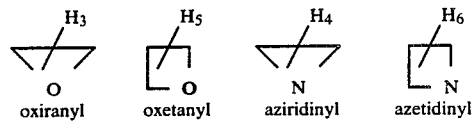

Examples of oxiranes, oxetanes, aziridines and azetidines having one or more substituent groups on their ring carbon atoms are: propyleneimine, propylene oxide, n-but-1-ene oxide, n-but-2-ene oxide, n-pent-2-ene oxide, n-hex-1-ene oxide, n-hex-2-ene oxide, n-hex-3-ene oxide, styrene oxide, stilbene oxide, epichlorohydrin, butadiene monoepoxide, 3,3-dimethyloxetane, 3,3-(pentamethylene)-oxetane, 2-propyl-3-ethyloxetane, and 3-hydroxyoxetane.

When the heterocyclic strained ring compound is selected from aziridines and azetidines, it is preferably selected from the group N-substituted aziridines and N-substituted azetidines, because by reacting this preferred group of compounds in accordance with the process of the present invention there are produced high energy material containing both nitrate ester ($-ONO_2$) and nitramine ($>NNO_2$) substituents. This is an important class of high energy material the members of which are generally more difficult to prepare by conventional known techniques than those which contain —ONO₂ substituents without >NNO₂ substituents. The terms N-substituted aziridines and N-substituted azetidines encompasses compounds which are substituted in either one or in two or more positions on the heterocyclic ring of the hetero-cyclic compound, provided the compounds are always substituted in the N-position. The heterocyclic ring of the preferred N-substituted aziridines and azetidines may be substituted by any group or proups.

Examples of N-substituent groups on the preferred N-substituted aziridines and azetidines include the following: halo, nitro, cyano or, preferably, an N-compatible organic radical.

The N-compatible organic radical may be optionally-substituted aliphatic, alicyclic or aromatic. The term aromatic used here encompasses, for the purpose of this specification, all aromatic and heteroaromatic radicals, based on carbon or otherwise, which contain $(4n+2)\pi$ electrons where n is zero or an integer. Aromatic radicals are preferably from the benzene and the monocyclic heteroaromatic series, and examples include phenyl, phenylene, pyridinyl, pyrimidyl, triazinyl ($—C_3N_3H_2$) and cyclotriphosphaza —1,3,5, —trienyl ($—P_3N_3H_5$). Aliphatic radicals are preferably from the alkyl, alkoxyl, alkenyl, ether, aldehydo, keto, acyl, alkoxy carbonyl, secondary or tertiary amino, amido (carbamyl, $—CONH_2$), oxamide residue ($—COCONH_2$) and guanidine residue ($—C(NH_2)=NH$) series containing up to 10, more preferably up to 5, carbon atoms, and examples include vinyl, ethyl, n-butyl and $—COOC_2H_5$. Alicyclic radicals are preferably either homocyclic containing from 4 to 8 carbon atoms, such a cyclohexyl, or heterocyclic containing 3 to 8 ring atoms, especially 3 or 4 ring atoms, such as oxiranyl, oxetanyl, aziridinyl or azetidinyl, provided that aziridinyl and azetidinyl radicals are either N-substituted or are attached through their N-ring atoms to the heterocyclic strained ring nucleus. The N-compatible organic radical may be monovalent and attached to the single N-atom on the aziridine or azetidine nucleus, or it may be polyvalent and attached to the N-atoms on two or more aziridine or azetidine nuclei. Examples of polyvalent organic radicals from the series given above are: carbonyl ($>C=O$), dicarbonyl ($—COCO—$), optionally-substituted phenylene, optionally-substituted $—(C=N-H)—$, triazine nucleus ($C_3N_3$) and cyclotriphosphaza-1,3,5-triene ($P_3N_3$) nucleus.

Examples of substituents for the aromatic N-compatible radicals are alkyl, alkenyl, alkoxyl, alkylthio, and halo (especially chloro), nitro and cyano substituted derivatives thereof, tertiary amino, azido, halo (especially chloro), nitro, cyano, and optionally-substituted oxiranyl, oxetanyl, aziridinyl and azetidinyl provided that aziridinyl and azetidinyl substituents are either N-substituted or are attached to the aromatic radical through their N ring atoms. Most preferably, the aromatic radical is either from the benzene series, especially phenyl, which is substituted by one or more substituents selected from nitro, N-arizidinyl and N-azetidinyl, or is from the monocyclic heteroaromatic series, especially $C_3N_3H_2$ or $P_3N_3H_5$, which is substituted by one or more substituents selected from N-aziridinyl and N-azetidinyl. Examples of substituents for the N-compatible aliphatic and alicyclic radicals are alkoxy, halo (especially chloro), cyano, azido, nitro, divalent oxy substituting adjacent carbon atoms on the radical, aryl, tertiary amino, and optionally-substituted oxiranyl, oxetanyl aziridinyl and azetidinyl provided that aziridinyl and azetidinyl substituents are either N-substituted or are attached to the aliphatic or alicyclic radical through their N ring atoms. Primary amino groups ($—NH_2$) on the aliphatic radicals are preferably substituted with divalent optionally substituted 1, M linked n-$C_M$ alkane alkane bridging groups where M is 2 or 3, which converts these amino groups into optionally substituted N-aziridinyl (M=2) or N-azetidinyl (M=3) substituent groups. In these substituents, the alkyl and alkenyl groups preferably contain up to 10, and more preferably up to 5, carbon atoms, and the oxiranyl, oxetanyl, aziridinyl and azetidinyl groups are, when substituted, preferably substituted by at least one group selected from halo, cyano, nitro hydroxy, azido, or $C_1$-$C_5$ alkyl optionally substituted with cyano, nitro, azido, halo or hydroxy.

Examples of aziridines and azetidines which are N-substituted with monovalent radicals are:

2-aziridineethanol, N-(2-cyanoethyl)-2-methylaziridine, N-(2-cyanoethyl)-aziridine, N-(n-butyl)-aziridine, N-picrylaziridine, ethyl-N,N-ethylenecarbamate, N-propyl-N,N'-propyleneurea, N-nitro-N',N'-propyleneguanidine, and N-(2-cyanoethyl)-azetidine.

Examples of reactive N-substituent groups on aziridines and azetidines which are preferably to be avoided are those consisting of or containing unsubstituted aryl (eg phenyl), hydroxyl, primary or secondary amines, and/or primary imines (>NH) since their use in present process tends to result in the formation of nitrate ester products which are generally impure and produced in low yield. Indeed, it is for this principal reason that N-substituted aziridines and azetidines are preferred over their N-unsubstituted counterparts, because the latter are by definition secondary amines (or primary imines) whereas the former are tertiary amines (or secondary imines).

In one preferred aspect of the present process, the strained ring compound contains at least two radicals per molecule selected from optionally-substituted oxiranyl, optionally-substituted oxetanyl, optionally-substituted N-aziridinyl and optionally-substituted N-azetidinyl, in which case the amount of nitrogen oxide employed in the present process is preferably at least equivalent to the number of these radicals present in the strained ring compound. The radicals may be the same or different, but are preferably the same.

Examples of aziridines and azetidines containing more than one N-aziridinyl or N-azetidinyl nucleus per molecule are: diethyleneoxamide, dipropyleneurea, and N-phenyl-N',N"-diethyleneguanidine.

One preferred class of heterocyclic strained ring compound comprises a poly-substituted aromatic compound wherein at least two of the sustituent radicals on the aromatic nucleus are strained ring heterocyclic groups A selected from the class consisting of an optionally substituted oxiranyl, oxetanyl, N-aziridinyl and N-azetidinyl. The at least two monovalent strained ring heterocyclic groups A are preferably the same. Examples of substituents for each group A are alkyl, alkenyl, alkoxyl, and alkylthio, and halo, hydroxy, nitro, azido, and cyano derivatives thereof, especially those containing up to 10, preferably up to 5 carbon atoms, aryl, halo, nitro, cyano, azido, hydroxyl, amido, especially tertiary amido, and amino, especially tertiary amino. More preferably, each group A is either unsubstituted or is substituted by a single $C_1$-$C_5$ alkyl, especially methyl, group. The aromatic radical is preferably selected from the monocyclic homoaromatic, especially benzene, series and from the monocyclic heteroaromatic series, and may be additionally substituted by substituent groups other than A. Examples of substituent groups other than A for the aromatic radical are alkyl, alkenyl, alkoxyl, and alkylthio, and halo, nitro and cyano substituted derivatives thereof, especially those containing up to 5 carbon atoms, aryl, especially phenyl, halo, nitro, cyano, carboxyl, carboxylate ester, hydroxyl and amino, especially tertiary amino. The aromatic radical is preferably substituted with a total of from 2 to 6 substituent groups.

When the aromatic radical is from the benzene series, the heterocyclic strained ring compound preferably comprises a compound of general formula I

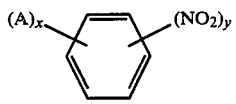

wherein A is defined above, x is an integer from 2 to 4, especially from 2 to 3, and y is 0 or an integer from 1 to (6-x). A is preferably an optionally-substituted N-aziridinyl or N-azetidinyl group, and is most preferably optionally-substituted N-aziridinyl. An example of a compound within the scope of general formula I is 2,4,6-trinitrobenzene substituted in each of its 3- and 5-ring positions by an N-aziridinyl group.

When the aromatic radical is from the heteroaromatic monocyclic series, the heterocyclic strained ring compound is preferably of general formula II

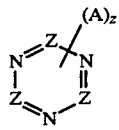

wherein Z is an atom of valency $n^1$, $n^1$ is 4 or 5, A is as defined above, and z is an integer from 2 to $3(n^1-3)$. Z is most preferably $C(n^1=4)$ or $P(n^1=5)$. A is preferably an optionally-substituted N-azetidinyl or N-aziridinyl group, most preferably optionally-substituted N-aziridinyl. Examples of novel compounds from this group are N,N,N',N',N'',N''-triethylenemelamine, 2,4,6-tris-(1'-azetidinyl)-1,3,5-triazine, and 2,2,4,4,6,6-hexakis- (1'-aziridinyl) cyclotriphosphaza-1,3,5-triene (compounds XXIV, LXXVI and LXXX whose structures are given in Table 3 below).

In a further preferred embodiment of the present process, the strained ring compound is an optionally-substituted oxirane comprising an expoxidised form of an optionally-substituted cyclene, especially a cyclene containing m ring carbon atoms and from 1 to m carbon-carbon double bonds where m is from 2 to 6, in which at least one of the ethylenically unsaturated groups of the cyclene is replaced by an expoxy group. Exampes of suitable epoxidised cyclenes are 1,2-epoxycyclohexane, 1,2,3,4,5,6-triepoxycyclohexane, and 1,2,5,6-diepoxycyclooctane. Where the expoxidised cyclene contains more than one epoxy group, then one or more of these groups may be cleaved in accordance with the present method depending on the amount of nitrogen oxide employed, to yield corresponding vicinal diol dinitrate groups. Typical fully nitrated products which may be prepared from the specific epoxidised cyclenes referred to above are cyclohexane-1,2-diol dinitrate, cyclohexane-1,2,3,4,5,6-hexol hexanitrate, and cyclooctane-1,2,5,6-tetrol tetranitrate respectively. Those products prepared from epoxidised cyclenes containing two or more epoxy groups represent a novel and (when fully nitrated) a highly nitrated and energetic class of compound which may be useful as primary or secondary explosives.

In another preferred embodiment of the present invention, the heterocyclic strained ring compound comprises a substituted oxirane or oxetane having each of one or more of its heterocyclic ring carbon atoms linked to an organic radical which is substituted by at least one oxy-radical capable of conversion to a nitrate ester group when reacted with an appropriate nitrating agent. The organic radical may be an aliphatic, alicyclic or aromatic radical and is preferably an aliphatic radical especially from the alkoxyl, alkyl and alkenyl series containing up to 6 carbon atoms. The one or more heterocyclic ring carbon atoms will normally be linked to a carbon atom on the organic radical. The organic radical may be divalent and attached to adjacent carbon atoms on the heterocyclic ring so that these carbon atoms and the organic radical together form a cyclic group for example cyclohexane. Preferably, however, the organic radical is monovalent and attached to a single carbon atom on the heterocyclic ring, in which case there may be more than one of the said organic radicals per heterocyclic molecule which may be the same or different. More preferably, however, there is only one of the said organic radicals per heterocyclic strained ring molecule. Other members of the ring are optionally-substituted by suitable radicals for carbon atoms, epecially $C_1-C_5$ alkyl, discussed earlier in this specification.

The organic radical is preferably substituted by not more than two, and most preferably only one, oxy-radical capable of conversion to nitrate ester groups. The oxy radical is most preferably a hydroxy (OH) radical because the OH radical may be readily converted to a nitrate ester ($-ONO_2$) group on reaction with concentrated $HNO_3$, with a concentrated $HNO_3/H_2SO_4$ mixture, or with $N_2O_5$. Other less preferred radicals are ester groups (—OOCR) where R is an optionally-substituted alkyl, especially $C_1-C_5$ alkyl, group or an optionally substituted aryl group. Most preferably, the organic radical in its oxy-radical substituted form is a hydroxy-substituted $C_1-C_3$ alkyl group, especially —$CH_2$—OH.

Examples of especially preferred heterocyclic stained compounds for use in this one further preferred aspect of the present invention are (a) 3-hydroxy-propene oxide (glycidol) and (b) 3-methyl-3-(hydroxymethyl) oxetane.

The molar ratio of nitrogen oxide, particularly $N_2O_5$, to heterocyclic compound in this further preferred aspect of the present invention is preferably at least $(a^1+a^2):1$ where $a^1$ is the total number of oxiranyl and/or oxetanyl groups per heterocyclic molecule and $a^2$ is the number of oxy-radicals per hetercyclic molecule that are capable of conversion to nitrate ester groups. This minimum ratio of nitrogen oxide to heterocyclic compound ensures that, in theory, the product will be fully nitrated and contain $(2a^1+a^2)$ nitrate ester groups per molecule with no residual heterocyclic strained rings or oxy-radicals remaining, although in practice in order to achieve full nitration a 10–20% amount of nitrogen oxide in excess of this minimum may be required. For example, the fully nitrated products from the two most preferred strained ring compounds (a) and (b) above are the known explosives nitroglycerine (from (a)) and metriol trinitrate (from (b)). When the amount of nitrogen oxide employed is less than $(a^1+a^2)$ moles per mole of hetercyclic strained ring compound, then the reaction will generated, in part at least, a partly nitrated product whose structural formula will depend upon the relative reactivity of the nitrogen oxide towards the oxyradical and the heterocyclic ring. The order of reactivity of the groups oxiranyl, oxetanyl, and hydroxyl towards the nitrogen oxide (especially $N_2O_5$) tends to be oxiranyl>hydroxyl>oxetanyl. A substituted oxetane having an OH-substituted organic radical will therefore normally require a ratio of nitrogen oxide to oxetane of more than $(a^2)$:1 to ensure that at least some residual nitrogen oxide is present, after the conversion of hydroxyl groups to nitrate ester groups, to react with the oxetane rings. A substituted oxirane containing an OH-substituted organic radical will in theory require a mole ratio of nitrogen oxide to oxirane of up to $a^1$:1 to ensure partial to complete raction of all oxiranyl groups and from $a^1$:1 to $(a^1+a^2)$:1 to ensure complete reaction of all oxiranyl groups and partial to complete conversion of all hydroxyl groups For example, when the heterocyclic compound is glycidol, the optimum molar ratio of the nitrogen oxide (which is preferably $N_2O_5$) to glycidol in the reaction mixture for the production of glycerol-1,2-dinitrate is from 1:1.1 to 1:0.9. Additional nitration of the OH radical to produce nitroglycerine may be suppressed by ensuring that a significant molar excess of $N_2O_5$ is avoided when the reactants are mixed. This may be achieved, for example, by slowly adding the $N_2O_5$ to excess glycidol in solution until the desired molar ratio is achieved.

Nitroglycerine is produced when the $N_2O_5$ and glycidol are reacted together in a ratio of more than 1 mole of $N_2O_5$ per mole of glycidol. The preferred molar ratio of glycidol: $N_2O_5$ in the reaction mixture for nitroglycerine production is from 1:1.8 to 1:2.2, although ratios of more than 1:2.2 will also give rise to high nitroglycerine yields. Small amounts of nitric acid byproduct are liberated. Conversely, although the reaction of 1 mole of 3-methyl -3-(hydroxymethyl) oxetane with more than 1.0 moles, preferably at least 2 moles most preferably at least 3 moles, of $N_2O_5$ produces corresponding trinitrate (metriol trinitrate), when a lower concentration of $N_2O_5$ is employed (1.0 moles or less) only the corresponding oxetane monomitrate is produced.

Small quantities of nitric acid or unwanted nitrate ester byproducts will be produced by nitrating the oxy radical or radicals with the nitrogen oxide. However, the problems associated with the separation and disposal of these byproducts are generally less severe than with conventional mixed acid nitration of polyols, because the quantities of acidic byproduct generated by the present process are usually much smaller and are more easily separated from the product (by, for example, washing the product with an aqueous, especially alkali, solvent).

One preferred class of substituted oxiranes which is suitable for use in the present process invention are polyepoxides having an average of two or more 1,2-epoxy groups per average molecular weight. Among the polyepoxides which can be used herein are the polyglycidyl ethers of polyphenols, such as Bisphenol A. These may be attained, for example, by etherification of a polyphenol with epichlorohydrin or dichlorohydrin in the presence of an alkali. The phenolic compound may be 2,2-bis(4-hydroxyphenyl)propane, 4,4'-dihydroxybenzophenone, 1,1-bis(4-hydroxyphenyl)ethane, 2,2-bis(4-hydroxy -tertiarybutylphenyl)propane, bis(2-hydroxynaphthyl)methane or 1,5-dihydroxynaphthalene. The polyphenol can also be a novolak resin.

Examples of this class of polyepoxides are the reaction products of Bisphenol A and epichlorohydrin.

Also suitable are the similar polyglycidyl ethers of polyhydric alcohols which may be derived from such polyhydric alcohols as ethylene glycol, diethylene glycol, triethylene glycol, 1,2-propylene glycol, 1,4-butylene glycol, 1,5-pentanediol, 2,4,6-hexanetriol, glycerol and trimethylolpropane.

Other examples of polyepoxides that may be used in this invention are the partial fatty acid esters of the above-mentioned glycidyl polyethers of polyhydric alcohols and glycidyl polyethers of polyhydric phenols. Linseed oil and castor oil are examples of fatty acids that may be used to produce these resins.

Also suitable are polyglycidyl esters of polycarboxylic acids which are produced by the reaction of epichlorohydrin or a similar epoxy compound with an aliphatic or aromatic polycarboxylic acid, such as oxalic acid, succinic acid, glutaric acid, adipic acid, azelaic acid, phthalic acid, isophthalic acid, terphthalic acid, 2,5naphthalenedicarboxylic acid and dimerized linolenic acid. Examples are diglycidyl adipate and diglycidyl phthalate, and similar esters.

Other examples are polyepoxides derived from the epoxidation of ethylenically unsaturated aliphatic or alicyclic compounds. The products of these epoxidation reactions include diepoxides and higher epoxides. These polyepoxides are non-phenolic and are obtained by epoxidation of polyolefins such as butadiene, for example, by oxygen and selected metal catalysts, by perbenzoic acid, by acetaldehyde monoperacetate, or by peracetic acid.

One especially preferred group of polyepoxides are epoxidised ethylenically-unsaturated polymers such as epoxidised polybutadiene, polyisoprene, or polydimethylbutadiene, or an epoxidised copolymer of butadiene or dimethylbutadiene with, for example, acrylonitrile. The polymer preferably has a molecular weight of at least 500 and/or at least 10 carbon-carbon double bonds before epoxidation, and preferably from 2% to 50%, most preferably from 10% to 40%, of its available ethylene bridging (>C=C<) groups are converted to epoxy groups during epoxidation. The epoxidised polymer, preferably epoxidised polybutadiene or an epoxidised copolymer of butadiene and acrylonitrile, may be functionally terminated with, for example, hydroxyl, carboxyl, or vinyl groups, and will most preferably have a molecular weight in the range 2000 to 10,000 in which case it may be a liquid rubber particularly if it is functionally terminated. Alternatively, the epoxidised polymer, preferably polybutadiene, may have a molecular weight in the range $10^4$ to $10^7$, preferably $10^4$ to $10^6$, in which case it will normally be a solid at room temperature. Prior to epoxidation, the polymer preferably contains up to 10,000, more preferably up to 1,000, most preferably up to 250, carbon-carbon double bonds.

The epoxidised polymers may, in accordance with the process of the present invention, be nitrated with just sufficient nitrogen oxide to cleave some or all of the epoxide groups to produce corresponding vicinal diol dinitrate (—CH(ONO$_2$)—CH(ONO$_2$)—) groups in the product, in which case the number of nitrate ester groups present in the product will be approximately twice the number of epoxy groups present in the epoxidised polymer starting material. In practice, a small proportion, typically 5-20%, of the nitrogen oxide will react with some of the remaining double bonds in the epoxidised polymer to produce vicinal C-nitro/nitrate ester (—CH(NO$_2$)—CH(ONO$_2$)—) groups in the product, so that a slight molar excess (typically 10-25%) of nitrogen oxide over that required for theoretical stoicheiometric reaction with all the available epoxy groups will normally be required to ensure that substantially all these epoxy groups are converted to vicinal diol dinitrate groups. When the molar ratio of nitrogen oxide to polymer is insufficient to ensure that all epoxy groups are converted, either the remaining epoxy groups may be retained to be utilised in, for example, a subsequent epoxy curing reaction to produce an energetic thermoset resin, or they may be destroyed by, for example, reaction with excess nitric acid to convert each remaining epoxy group into a vicinal hydroxy-nitrate (—CH(ONO$_2$)—CH(OH)—) group.

As an alternative to using a restricted amount of nitrogen oxide in the reaction with the epoxidised polymer, the epoxidised polymer may be nitrated with sufficient nitrogen oxide, in accordance with the process of the present invention, in order to nitrate all the epoxy groups and some or all of the remaining carbon-carbon double bonds in the polymer. A 50% epoxidised polybutadiene (that is to say a polybutadiene 50% of whose ethene bridging groups (—CH=CH—) are converted to epoxy groups) nitrated with excess nitrogen oxide equal to or in excess of that required to nitrate all epoxy and ethene bridging groups in the polymer will therefore, in accordance with the following equation, have a maximum of about 37½% of its carbon atoms substituted by nitrate ester (ONO$_2$) groups and a maximum of about 12½% of its carbon atoms substituted by nitrate (NO$_2$) groups:

double bond or hydrolyse a halo substitutent). Organic oxidants such as m-chloroperbenzoic acid have been found suitable for use in this subsequent oxidation step; however they have the disadvantage that they leave behind in the reaction mixture reduced organic residues (in the example given above, m-chlorobenzoic acid) which may contaminate the product and may be difficult to remove. The preferred oxidising agent is ozone which has been found capable of oxidising the nitrite in high yield and does not generally give rise to problems of product contamination.

The reaction, between heterocyclic compound and nitrogen oxide, may be performed in the gas phase provided the reaction conditions are moisture-free. Preferably, however, it is conducted in an anhydrous inert non-protonic (ie aprotic) solvent which has the advantage that the reaction is easier to control and may be performed at low-to-ambient temperatures. Avoidance of high reaction temperatures is particularly advantageous when using N$_2$O$_5$ as the nitrogen oxide, because high temperatures can lead to early onset of N$_2$O$_5$ decomposition. Any anhydrous organic or inorganic non-protonic solvent which does not react with either the starting materials or the reaction products of the present method may be employed. Preferably, however, it should also be possible to either dispose of or recycle the solvent simply, safely, and at little cost. Though inorganic nonprotonic solvents such as phosphorus oxychloride, sulphuryl chloride and liquid sulphur dioxide may be employed provided they sufficiently solubilise the strained ring compound, organic solvents, espically the halogenated alkanes, generally meet these criteria and are therefore preferred. Chlorinated and/or fluorinated alkanes are especially preferred. Examples of suitable organic solvents are dichloromethane, chloroform, carbon tetrachloride, and Freons (chlorofluorocarbons) with boiling points preferably above 20° C. at atmospheric pressure. Nitromethane, sulpholane,

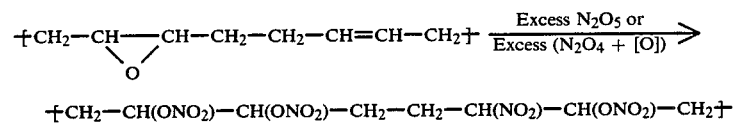

+CH$_2$—CH(ONO$_2$)—CH(ONO$_2$)—CH$_2$—CH$_2$—CH(NO$_2$)—CH(ONO$_2$)—CH$_2$+

The nitrated polymers which are described above are novel materials which may be used as or within energetic plastic or rubbery binding material in composite rocket propellant compositions. One advantage of nitrating the aforementioned functionally-terminated, especially hydroxy terminated, epoxidised polybutadiene liquid rubbers is that because the nitrogen oxide is generally less reactive towards the functional terminal groups than towards the epoxy groups, nitrated polymers can be prepared from these epoxidised polymers with their terminal groups at least partly intact. The terminal groups can therefore still be utilised in subsequent curing reactions.

When the present heterocyclic strained ring compounds are reacted with dinitrogen pentoxide the required high energy materials are obtained without further treatment of the reaction mixture. However, when the present heterocyclic compounds are reacted with dinitrogen tetroxide the required high energy materials are only obtained after subsequent oxidation of the resultant X-nitrate substituent or substituents. Preferably, the oxidising agent selected for use in this subsequent oxidation step has no effect on any other part of the intermediate nitrite compound (eg does not oxidise a and acetonitrile may also be used.

When the present process is conducted in the gas phase, the temperature during the reaction with the nitrogen oxide will be selected to ensure the heterocyclic strained ring compound is above its boiling point at the reaction pressure employed. Preferably, however, this temperature will not exceed 250° C. When inert solvents are employed, the process may be conducted at high temperature (up to the boiling point of the solvent or mixture of solvents) and/or pressure. In this case however, it is preferred to allow the reaction within the solvent or mixture of solvents to proceed at low-to-ambient temperatures ($-20°$ to $+30°$ C., especially $-10°$ to $+10°$ C.) and atmospheric pressure.

Generally the present process proceeds very quickly at ambient temperature and pressure when conducted in an inert solvent. In a few cases, however, the process, as described above, may be rather slow and it may be necessary to increase the rate of reaction. This may be done by increasing the reaction temperature to above ambient; alternatively the reaction may be accelerated by the presence of a Lewis acid such as aluminium chloride or stannic chloride.

The reaction time, between heterocyclic strained ring compound and nitrogen oxide, is not critical and will normally be adjusted in accordance with the period required to obtain complete reaction between these reactants. It is preferred however, especially when oxiranes are being reacted with the nitrogen oxide, not to leave the reactants in contact with one another for too long a period because this can lead to some product polymerisation, hence reduction in product purity and yield, especially when the nitrogen oxide is $N_2O_4$. For this reason, the reaction time between the oxirane and the nitrogen oxide is preferably not more than 2 hours, most preferably not more than 30 minutes, after which time the product will either be isolated (when the nitrogen oxide is $N_2O_5$) or will be oxidised, preferably in situ (when the nitrogen oxide is $N_2O_4$). Other ways of suppressing product polymerisation include employing an excess of nitrogen oxide in the reaction mixture, typically an excess of at least 5% over that required for stoichcometric reaction with the strained ring compound, and adding strained ring compound to the nitrogen oxide (rather than the reverse operation) until the required molar ratio of reactants is present in the reaction mixture.

After preparation, the final product is preferably treated with a base, more preferably an inorganic base, to neutralize any acidity in the product resulting from the process. The removal of acidity, if present, generally improves the stability and/or purity of the final product.

According to further aspects of the present invention there are provided several novel nitrate esters which are products of the process of the first aspect. In one of these aspects, there is provided the group of novel nitrated polymers which have been described earlier in this specification. They generally have molecular weights of from 500 to $10^6$. In another further aspect of the present invention there is provided a novel high energy nitrated aromatic compound comprising an aromatic nucleus substituted by at least two organic nitrate ester radicals B which may be the same or different, and, optionally, by one or more radicals other than B, wherein each radical B comprises a group of formula $[O_2NO]_p$$[N(NO_2)]_q$-Y-ONO$_2$ wherein p and q are independently 1 or 0, (p+q)=1, Y is an optionally substituted 1,M-linked straight chain $C_M$-alkane bridging group which is divalent when q is 1 and trivalent when p is 1, and M is 2 or 3. Therefore by definition, each radical B comprises one of the following structures:

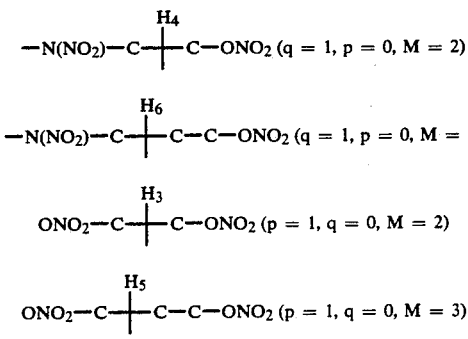

This novel class of nitrated aromatic compounds may be prepared by reacting a corresponding aromatic compound, comprising an aromatic group substituted by at least two radicals selected from aziridinyl, azetidinyl, oxiranyl and oxetanyl, with a nitrogen oxide in accordance with the process of the first aspect of this invention. Their principal advantage is that they provide alternative aromatic-based high energy materials (especially explosives) to compounds such as TNT, picric acid and pentryl, which contain at least 4 nitro groups, in the form of nitramine and/or nitrato groups, per aromatic nucleus.

The at least two radicals are preferably the same. When at least one of the radicals B is $B^3$ or $B^4$, then the $B^3$ or $B^4$ radical may be attached through any one of its available substituent positions on Y to the aromatic group. However, when one of the groups B is $B^1$ or $B^2$, it is linked to the aromatic ring through its available nitramine nitrogen atom (—N(NO$_2$)—) so that Y is divalent. Examples of substituents for each bridging group Y are alkyl, alkenyl, alkoxyl and alkythio, and halo, hydroxy, azido, nitro, and cyano derivatives thereof, especially those containing up to 10, preferably up to 5 carbon atoms, aryl, azido, halo, nitro, cyano, hydroxyl, amido, especially tertiary amido, and amino, especially tertiary amino. More preferably, each bridging group Y is either unsubstituted or is substituted by a single $C_1$-$C_5$ alkyl, especially methyl, group. Especially preferred groups Y are —CH$_2$.CH$_2$—, —CH(CH$_3$)—CH$_2$—, and —CH$_2$.CH(CH$_3$)— when B is $B^1$ or $B^2$, and >CH.CH$_2$—and >CH.CH(CH$_3$)— when B is $B^3$ or $B^4$.

The aromatic nucleusis preferably selected from the monocyclic homoaromatic, especially benzene, series and from the monocyclic heteroaromatic series, and may be additionally substituted by substituent groups other than B. Examples of substituent groups other than B for the nucleus are alkyl, alkenyl, alkoxy, and alkylthio, and halo, nitro and cyano substituted derivatives thereof, especially those containing up to 5 carbon atoms, aryl, especially phenyl, halo, nitro, cyano, carboxyl, hydroxyl and amino, especially tertiary amino. The nucleus is preferably substituted with a total of from 2 to 6 substituent groups.

When the nucleus is from the homoaromatic benzene series, the nitrated aromatic compound may have the general formula III

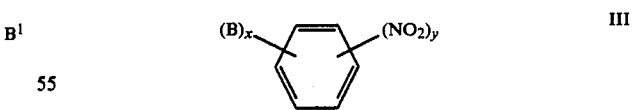

wherein B is as defined above, x is an integer from 2 to 4, especially from 2 to 3, and y is 0 or an integer from 1 to (6-x). B is preferably optionally-substituted $B^1$ or $B^2$, and is most preferably optionally-substituted $B^1$. An example of a compound within the scope of general formula VI is 2,4,6-trinitrobenzene substituted in each of its 3-and 5- ring positions by the group (—N(-NO$_2$)CH$_2$CH$_2$ONO$_2$).

When the nucleus is from the heteroaromatic monocyclic series, the nitrated organic compound is preferably of general formula IV

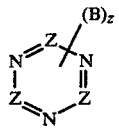

IV wherein Z is an atom of valency $n^1$, $n^1$ is 4 or 5, B is as defined above, and z is an integer from 2 to $3(n^1-3)$. Z is most preferably C ($n^1=4$) or P($n^1=5$). B is preferably optionally-substituted $B^1$ or $B^2$, and is most preferably optionally-substituted $B^1$. Examples of novel compounds from this group are the trinitramine trinitrate derivatives of N,N,$N^1$,$N^1$,N'',N''-triethylenemelamine and of 2,4,6-tris-(1-azetidinyl)-1,3,5-triazine, and 2,2,4,4,6,6-hexakis-(2'-hidroxyethylnitroamino) cyclotriphosphaza-1,3,5-triene hexanitrate (compounds XXVIII, LXXVIII and LXXXI whose structures are given in Table 4 below).

One further potentially useful group of novel organic nitrates which may be prepared by the process of the present invention are organic nitrate esters containing at least one epoxide (oxiranyl) group and at least one vicinal di(methylene nitrate ester) (—CH(ONO$_2$)—CH(ONO$_2$)—) group. These may be prepared by reacting a poly. epoxide with a nitrogen oxide in accordance with the process of the first aspect of the present invention, provided that at least one epoxide group remains unreacted per molecule of polyepoxide starting material. This may be ensured by providing a molar excess of epoxy compound in the reaction mixture such that the mixture contains insufficient nitrogen oxide to react with all the available epoxide groups. Not only are these novel epoxy-nitrates high energy materials in their own right, they may also be used to prepare energetic thermoset resin by curing them with conventional epoxy resin hardners, particularly when the number of epoxy groups remaining per molecule of epoxy-nitrate is more than one and is preferably two.

The novel epoxy-nitrates according to the aspect of the present invention cannot be prepared by the conventional mixed acid nitration of the corresponding compounds in which the nitrate ester groups are replaced by —OH groups, because epoxy groups are acid sensitive and are readily converted to vicinal hydroxy-nitrate (—CH(OH)CH(ONO$_2$)—) groups on reaction with nitric acid.

An example of a novel epoxy-nitrate according to this aspect of the present invention is 1,2-epoxybutane-3,4-diol dinitrate.

The present method will now be described by way of Example only.

Reagents

All chemicals were used as received unless otherwise stated. Starting materials were supplied as follows: acrylonitrile, and triethylamine -1,2-diol as British Drug Houses Ltd (BDH) reagent grade; N-(n-butyl)-ethanolamine [2-butylaminothanol], cyanuric chloride and propyleneimine from Fluka AG ("purum" grade); oxalyl chloride (98%) from Aldrich Chem. Co. Ltd; and 2chloroethylamine hydrochloride from Lancaster Synthesis Ltd. 2-Aziridineethanol was supplied by Aldrich Chemical Co (reagent grade).

Commercially available epoxides, except for propylene oxide and glycidol, were Aldrich reagent or Gold Label (but-1-ene oxide) grade and were used as received, with the exception of butadiene diepoxide which was distilled before use (b.p. 56°-8° C./25 mm Hg). Propylene oxide and glycidol were supplied by BDH Chemicals Ltd, Poole, UK. The former was distilled prior to use (b.p. 35°C.), and the latter used as received.

Other starting materials were supplied as follows: alkenes (except but-2-ene and pent-2-ene) from Aldrich (Gold Label grade; but-2-ene, benzene and toluene, from BDH (reagent grade); and pent-2-ene from Fluka But-2-ene was supplied as a compressed gas and was used as received. The liquid alkenes were likewise used as received.

Arco polybutadiene BD resin Grade R45M, a hydroxy-terminated polybutadiene liquid prepolymer, was supplied by Atlantic-Richfield Chemical Co, USA. It has a molecular weight of about 2,500 (about 50 butadiene units hence carbon-carbon double bonds per chain) and an OH functionality of about 2.2.

Amberlite resin IR120 was obtained in its Na-form from BDH. This was converted to its H-form before use by stirring with an excess of 5M hydrochloric acid and then washing with distilled water until free from acid.

Hydrogen peroxide (60% w/v, equivalent to 50% w/w) was supplied by BDH and stored at 0° C. before use.

Potassium flouride from BDH was "activated" before use by heating at 120° C. for 2 hours in vacuo and stored in a desiccator.

Dinitrogen tetroxide ($N_2O_4$) was supplied as a liquid under pressure in cylinders from BOC Special Gases Division, London, SW19, and was used as received.

Oxetane, 3,3-dimethyloxetane, and 3-methyl-3-(hydroxymethyl) oxetane [3-methyl-3-oxetanemethanol] were supplied by Aldrich (reagent or ABC grade respectively); they were distilled from $CaH_2$ before use.

Solvents and other inorganic reagents were all supplied by BDH (reagent grade) with the following exceptions: phosgene was supplied by BDH, Poole, UK as a ca 12.5% w/w solution in toluene, chlorosulphonic acid (99%) was supplied by Aldrich Chem. Co. Ltd, dichloromethane was hplc grade (BDH) and was dried by passage through a column of chromatographic silica gel (BDH) before use; methanol, acetonitrile and water used in hplc (high pressure liquid chromatograph) separations were Fisons hplc grade (acetonitrile was "Far U.v." grade); 95% ethanol was supplied by Burroughs Ltd; CDCl$_3$ and D$_6$-acetone by Aldrich (99.5% isotopic purity). CDCl$_3$, benzene and toluene were all allowed to stand over 4A molecular sieves (BDH) before use.

The preparations of other reagents used in the Examples and elsewhere are described below. The products of the preparations were characterised by their $^1$H nmr (nuclear magnetic resonance), $^{13}$C nmr and ir (infra red) spectral data. Other measurements which were also made occasionally included mas spectral, gas-liquid chromatography (glc), high pressure liquid chromatography (hplc), thin layer chromatography, and melting point measurements.

1. Preparation of Dinitrogen Pentoxide ($N_2O_5$)

$N_2O_5$ may be prepared by the oxidation of dinitrogen tetroxide ($N_2O_4$) with ozone. Because of the thermal instability of $N_2O_5$, during the preparation and subsequent use the temperature should not exceed 30° C. and preferably operations are carried out between −10° C. and 20° C. All operations must be caried out under anhydrous conditions since $N_2O_5$ is readily hydrolysed to nitric acid. For the reactions described here it is convenient to dissolve the $N_2O_5$ in an inert solvent, such as a chlorinated alkane.

An ozone/oxygen mixture, from a commercially available ozoniser was passed into a glass vessel containing $N_2O_4$. Oxidation occurs in the gas phase and the resulting $N_2O_5$ is carried in the oxygen stream and trapped in a series of cold traps kept at $-20°$ to $-30°$ C. Any unreacted $N_2O_4$ is subsequently reacted by resubliming the initial trapped product in an ozonised oxygen stream. The pure, white crystals of $N_2O_5$ can be stored at $-78°$ C. for at least 7 days before use without any noticeable decomposition.

2. Preparation of ethyleneimine

Ethyleneimine was prepared by the method of Wystrach (*J Am Chem Soc* (1956), 78, 1263)

3. Preparation of 2, 4, 6-trinitroanisole 2, 4, 6-Trinitroanisole was prepared by the method of Urbanski ("Chemistry and Technology of Explosive" Vol 1, p 547 (Pergamon, 1964)).

4. Preparation of N-(2-Cyanoethyl)-2-methylaziridine (XVII)

Propyleneimine (28.5 g, 0.5 mol) and acrylonitrile (50 ml, ca 50% molar excess) were heated together under reflux for 40 hr. The mixture was then fractionated under vacuum to give the compound XVII (35.5 g, 64.5%) as a colourless oil, bpt (boiling point) 95°–7° C./95 mbar, which had the expected ir and $^1H$ nmr spectra.

5. Preparation of N-(2-cyanoethyl)-aziridine (XVIII)

Ethyleneimine was reacted in a manner similar to that given in Preparation (5) above, to give N-(2-cyanoethyl)-aziridine, bpt 55°–6° C./8 mbar, in accordance with the method of Bestian (*Annalen* (1950), 566, 210–244).

6. Preparation of N-(n-butyl)-aziridine (XIX)

Compound XIX was prepared from N-(n-butyl)-ethanolamine and chlorosulphonic acid in 30% yield, bpt 29°–30° C./95 mbar, in accordance with the method of Elderfield et al (*J Org Chem* (1949), 605–637). $^1H$ nmr and ir spectra were in agreement with the assigned structure.

7. Preparation of N-Picrylaziridine (XXIII)

Compound XXIII was prepared by a modified version of the method of Bestian (qv). Anhydrous ethyleneimine (1.66 g) in methanol (10 ml) was added dropwise over 20 minutes with stirring at room temperature to a solution of trinitroanisole (10.0 g) in the same solvent (100 ml). A thick precipitate formed half-way through the addition, and after stirring for 2 hr (after which time thin layer chromatograms (tlc) ($CH_2Cl_2$) showed some unchanged trinitroanisole) further ethyleneimine (0.3 g) was added. Further stirring was continued for an additional 0.5 hr, and tlc indicated the absence of trinitroanisole. The precipitate was filtered off to give 8.70 g of N-picrylaziridine, the $^1H$ nmr of which indicated that it was contaminated with ca 10 mol % of trinitroanisole, the remaining signals being in agreement with structure XXIII. The net yield was thus 7.83 g (74%), and the product was used without further purification in the subsequent reaction owing to the possibility of thermal decomposition during recrystallisation.

8. Preparation of N,N,N',N',N'',N''-Triethylenemelamine (XXIV)

This material was prepared from 2-chloroethylamine hydrochloride/KOH and cyanuric chloride in aqueous dioxane as described by Wystrach et al (*J Am Chem Soc* (1955), 77, 5915). The yield of triethylenemelamine (XXIV) was 86%, with $^1H$ & $^{13}C$ nmr and ir spectra consistent with the assigned structure.

9. Preparation of N,N,N',N',N'',N''-Tripropylenemelamine (XXV)

This corresponding tris-(2'-methyl) derivative (XXV) was prepared in an analogous manner to XXIV from cyanuric chloride and propyleneimine, as described by Schaefer (*J Am Chem Soc* (1955), 77, 5928–5930). Yield was 90%, mpt 97°–9° C. (from petroleum ether (bpt 60°–80° C.) containing a trace of toluene).

10. Preparation of N,N,N',N'-Diethyleneoxamide (XXXI)

A solution of oxalyl chloride (63.5 g, 0.5 mol) in toluene (150 ml) was added dropwise with vigrous stirring over 2 hr to a mixture of triethylamine (55.55 g, 0.55 mol) and ethyleneimine (43 g, 1.0 mol) in toluene (150 ml). The temperature of addition was maintained below 10° C. (ice water bath), but the addition had to be halted after approximately 70% of the oxalyl chloride solution had been added because of stiring failure owing to the heavy precipitate of triethylamine hydrochloride. The experiment was nevertheless continued, and the mixture was filtered through celite and the solvent removed on a rotary evaporator (30° C., 100 mbar). This gave a light brown liquid and a thick film of a resinous compound. Addition of ether (200 ml) to the flask caused the separation of 20 g (18.8%) of a fine white solid together with some of the resinous compound. This mixture of solids was filtered off and the ether evaporated. The mixture was dissolved in methanol and the resulting solution evaporated gently in air until a fine white precipitate appeared. The solid (0.75 g), mpt 130° C. was filtered off and dried; $^1H$ nmr and ir spectra indicated that this compound was the desired product XXXI, although still containing some impurities.

11. Preparation of Ethyl N,N-ethylenecarbamate (XXXIII)

A solution of ethyleneimine (23 g, 0.5 mol) and triethylamine (52 g, 0.55 mol) in toluene (200 ml) was added slowly with stirring and cooling (ice-water bath) to a solution of ethyl chloroformate (54 g, 0.5 mol) in toluene (400 ml). The temperature of the addition was maintained below 15° C. whilst the mixture was stirred at room temperature for 1.5 hr. The precipitate was then filtered off and the filtrate washed with water (400 ml) and dried over anhydrous sodium sulphate. The toluene was removed using a rotary evaporator (40° C., 100 mbar) leaving a light yellow oil. Distillation of this oil gave 15.4 g (28%) of XXXIII as a clear liquid, bpt 51.3°–52.0° C./ 25 mbar, which gave $^1H$ nmr and ir spectra consistent with the desired product.

12. Preparation of N,N,N',N'-dipropyleneurea (XXXVIII)

A solution of phosgene in toluene (12.5% w/w in 190 ml =24.5 g (0.25 mol) $COCl_2$) was added dropwise with rapid stirring over 2 hr to a mixture of triethylamine (52.5 g, 0.5 mol) and propyleneimine (28.5 g, 0.50 mol) in toluene (120 ml) at 10°–12° C. A thick white precipitate of triethylamine hydrochloride formed whilst stirring was continued for a further 30 min at the same temperature. The precipitate was then filtered off (Celite) and the filtrate concentrated under vacuum to give a mobile yellow oil. This gave, on bulb-to-bulb distillation, the desired propyleneurea derivative (XXXVIII) as a pale yellow oil (25.5 g, 37%), bpt 80°–95° C./ 0.8 mbar, identified from its ir and $^1$H nmr spectra.

13. Preparation of N-(n-propyl)-N',N'-propyleneurea (XXVII)

A solution of propyleneimine (25.5 g, 0.45 mol) in ether (30 mol) was added over 20 min with stirring and cooling (temperature below 20° C.) to a solution of n-propyl isocyanate (30.75 g, 0.375 mol) in the same solvent (100 ml). After a further period of stirring (1–1.5 hr) no isocyanate remained (ir). Removal of the solvent at high vacuum gave the crude urea (XXVII) as a pale yellow oil (43.5 g, 81.7%), which had ir and $^1$H nmr spectra consistent with the assigned structure. Purification of a portion by bulb-to-bulb distillation gave the pure urea as a colourless oil, bpt 120°–5° C./ 1.0 mbar. The high stability of the material was demonstrated by the fact that the urea remained unchanged (ir) on standing at ambient temperature for 8 months.

14. Preparation of N-nitro-N',N'-propyleneguanidine (XLVI)

2-Methyl-1(3)-nitro-2-isothiourea was prepared by nitration of 2-methyl-2-isothiouronium sulphate as described by Fishbein et al (*J Amer Chem Soc* (1954), 76, 1877–1879). Treatment of this material (6.75 g) with propyleneimine as described by Lowe et al (*J Org Chem* (1963) 28 1496–1498) gave N-nitro-N',N'-propyleneguanidine (3.9 g, 54%) with the correct melting point and ir spectrum.

15. Preparation of N-phenyl-N',N',N'',N''-diethyleneguanidine (XLVII)

Phenylisocyanide dichloride (19.1 g, 0.11 mol) in toluene (200 ml) was added dropwise with stirring and cooling (temperature 10°–15° C.) to a solution of ethyleneimine (10.75 g, 0.25 mol) and triethylamine (30.3 g, 0.30 mol) in the same solvent (200 ml). Stirring was continued at room temperature for 30 hr, then precipitated triethylamine hydrochloride was filtered off and washed with toluene. The combined filtrate and washings were evaporated (50 mbar, 30° C.) to give the compound XLVII as a light brown viscous liquid, 16.2 g (78.6%). Attempted distillation of a portion resulted in decomposition to a dark olive-green liquid which, from its $^1$H nmr spectrum, did not contain any aziridinyl groups. Accordingly, the crude product (identity verified by $^1$H & $^{13}$C nmr and ir spectra) was used in subsequent experiments, and, because of its thermal instability, it was stored at −40° C. until used.

16. Preparation of N-(2-cyanoethyl)-azetidine (LXXV)

Compound LXXV was prepared after the method of Chen et al (*Bull Chem Soc Jpn* (1967), 40, p1964). Azetidine (2.5 g, 45 mmol) in ether (20 ml) was added, with cooling to ensure that the temperature did not exceed 5° C., to a stirred solution of acrylonitrile (2.39 g, 2.98 ml, 45 mmol) in ether (20 ml). The mixture was stirred at room temperature overnight, then the solvent was removed to give compound LXXV (3.95 g, yield 80.7%) whose identity was verified by its $^1$Hnmr and its ir spectra. The product was found to be sufficiently pure to be usable in subsequent reactions.

17. Preparation of 2,4,6-tris-(1-azetidinyl)-1,3,5-triazine (LXXVI)

Compound LXXVI was prepared after the method of Schaefer (*J Am Chem Soc* (1955) 77 p592B). The hydrochloride salt of azetidine was reacted with cyanuric chloride in water to give compound LXXVI as a white solid (yield 78%) having a melting point of 225°–238° C. The $^1$Hnmr of this compound indicated that its identity was correct and that its purity was adequate for subsequent reactions without further purification.

18. Preparation of 2,2,4,4,6,6-hexakis-(1'-aziridinyl)cyclotriphosphaza-1,3,5-triene (LXXX)

This compound (also known as the phosphonitrilic trimer of apholate) was prepared by the method of R Katz et al, *Inorg. Chem.* (1964) 3, 757–761.

19. Preparation of but-2-ene oxide (CI), pent-2-ene oxide (CII), hex-1-ene oxide (CIII), hex-2-ene oxide (CIV), and hex-3-ene oxide (CV)

But-2-ene oxide and hex-1-,2-, and 3- ene oxides were synthesised from the corresponding alkenes by oxidation with m-chloroperoxybenzoic acid by using the general methods described below:

50 ml of dichloromethane containing 0.1 mole of alkene was placed in a magnetically stirred flask immersed in a water bath at 30° C. 0.15 mole m-chloroperoxybenzoic acid was then added and the reaction mixture stirred at constant temperature for 2 hours. Excess m-chloroperoxybenzoic acid and the m-chlorobenzoic acid generated by reaction were filtered off. The last traces of the organic acids remaining soluble in the medium were then removed by adding 200% molar excess of activated potassium fluoride heated for 1 hour at 100° C. under vacuum, (see Camps etal, Tetrahedron Lett., 22, (1981), p 3895), stirring for a further 2 hours and filtering off the complex formed. The solvent was removed on a rotary evaporator and the product characterised by nmr and ir spectroscopy and its purity checked by glc.

In order to investigate a method whereby the use of toxic potassium fluoride might be avoided, pent-2-ene oxide was prepared as follows by the method of Pasto and Cumbo (*J. Org. Chem.* 30 (1965), p 1271): Pent-2-ene (0.24 mol) was added with stirring at 5° C. to a solution containing a 10% molar excess of m-chloroperoxybenzoic acid in 500 ml of diethyleneglycol dimethyl ether (diglyme). The mixture was stirred for a further 2 hr at 5° C., then left overnight in the refrigerator. The crude produce was then separated from the acid/peracid solution by distillation, collecting the distillate (ca 150 ml) up to 161° C. Finally, pent-2-ene oxide (99% pure by $^1$H nmr) was isolated by redistillation through a 150 mm column packed with glass beads. Yield was 14.9 g (73%), b.p 82°–5°C.

20. Preparation of Epoxidised HTPB using Peracetic Acid

Epoxidised HTPB with varying degrees of epoxidation were prepared after the method of Zuchowska (*Polymer* (1980) 21,514). The active oxidant used was peracetic acid which is generated in situ from acetic anhydride and aqueous hydrogen peroxide. A strongly acid ion-exchange resin was also present as catalyst. Epoxidations were carried out using various ratios of catalyst and reagents (polymer, hydrogen peroxide and acetic anhydride) to determine optimum conditions for 20% epoxidation of the double bonds (20% epoxidation means 20% of the ethylenically-unsaturated groups in the HTPB starting material are converted to epoxide groups). These conditions are summarised in Tables 1 and 2 below. Such experiments were carried out on a small-scale (0.2 mole HTPB) but when the optimum experimental parameters had been ascertained then large scale preparations (up to 10 moles HTPB) of 20% epoxidised polymer were undertaken.

TABLE 1

Epoxidation of HTPB Using Peracetic Acid

| Base Molar Ratio HTPB:$H_2O_2$:$Ac_2O$ | Reaction Time (hours) | Epoxidation % |
|---|---|---|
| 1:1:0.5 | 2.0 | 23.2 |
| 1:2:0.5 | 2.0 | 28.0 |
| 1:2:1 | 2.0 | 24.7 |
| 2:2:0.5 | 2.0 | 28.5 |
| 1:1.2:0.5 | 2.0 | 30.0 |

*"Base Molar Ratio HTPB" refers to the concentration in moles of the butadiene repeat unit in the polymer.

TABLE 2

Effect of Catalyst on the Epoxidation of HTPB Using Peracetic Acid

| Reaction Time (hours) | Resin Added % | Epoxide Value % |
|---|---|---|
| 2 | 10 | 7.38 |
|   | 20 | 10.79 |
|   | 40 | 18 10 |
|   | 60 | 16.66 |
|   | 80 | 20.68 |
|   | 100 | 18.99 |
| 4 | 10 | 12.08 |
|   | 20 | 18.12 |
|   | 40 | 25.40 |
|   | 60 | 28.81 |
|   | 80 | 31.30 |
|   | 100 | 30.85 |

A description of a typical small-scale epoxidation procedure chosen to maximise production of 20% epoxidised HTPB is given below.

20.4 g (19 ml) Acetic anhydride was dissolved in an equal volume of dichloromethane in a three-necked flask fitted with a thermometer and stirrer, and immersed in a water bath at room temperature. 15 ml Hydrogen peroxide (60% w/v) was added and the mixture stirred vigorously. A condenser was attached to prevent loss of solvent caused by the generated heat, and the temperature was maintained at 35° C. 8 g Amberlite IRI20 (H form) resin was then added and, after 30 minutes, 10.8 g HTPB dissolved in 30 ml dichloromethane was introduced to the reaction mixture. The temperature was maintained at 40° C. throughout the 2 hours reaction time. The solution was then neutralised with excess sodium bicarbonate, filtered and dried over magnesium sulphate. The epoxidised polymer was isolated finally by removal of the solvent on a rotary evaporator.

Preparation of 2-propyl-3-ethyloxetane (CXXIII)

This compound was prepared after the method of Moulines et al, *Synthesis*, (1981), 550. 18 g 2-ethylhexae-1, 3-diol (Aldrich Chemical Co.) was dissolved in dry THF (350 ml) and the solution was chilled to −3° C. (ice-salt bath). n-Butyllithium solution (1.6M in hexane, 94 ml, 0.15 mol) was added dropwise with stirring over 45 minutes (temperature 5°±5° C.). Stirring was continued for a further 1 hour at room temperature, then p-toluenesulphonyl chloride (28.6 g, 0.15 mol) in dry THF (75 ml) was added dropwise over 45 minutes with cooling in an ice-bath. After a further period of stirring of 1 hour a second portion of n-butyl lithium (94 ml) was added over 30 minutes at 5°-10° C. (ice-bath cooling), and the mixture was stirred overnight at room temperature. Finally, the mixture was heated at 60°-65° C. for 2.5 hours (thick white suspension forms), prior to concentration in vacuo, addition of water (750 ml) and continuous extraction with ether for 4 hours. After removal of the ether the resulting pale yellow oil was distilled to give 5.25 g (33%) of (CXXIII), bp 70.4°-71.8° C./100 mbar.

Preparation of 3,3-(Pentamethylene)-oxetane (CXXII)

1,1-Bis-(Hydroxymethyl)-cyclohexane (21.6 g, 0.15 mol) prepared by a method after Backer and Winter, *Rec. Trav. Chim. Pays-Bas* 56 504 (1937), was treated as described above for the preparation of compound CVI except that a further 250 ml THF was added in the first step (to prevent formation of a gelatinuous precipitate), and continuous extraction was carried out over only 3 hours. The oxetane (CXXII) was isolated as a colourless oil, bp 59.5°-60.5° C./30 mbar, with net yield of 10.9 g (57%) boiling within the range 57.0°-60.5° C./30 mbar.

The structural formulae of selected reagents used in the following Examples are given in Table 3 below.

TABLE 3

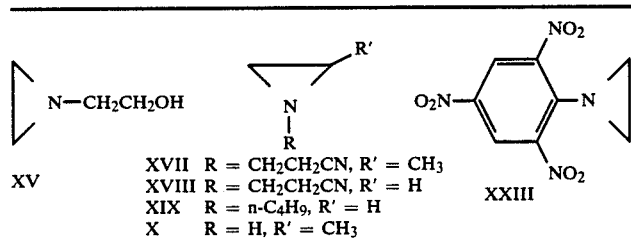

TABLE 3-continued
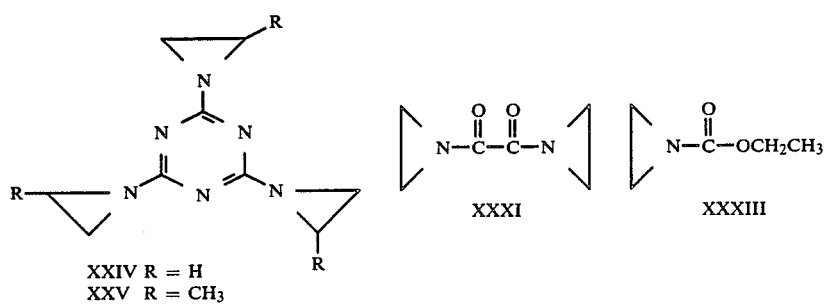
XXIV R = H
XXV R = CH₃
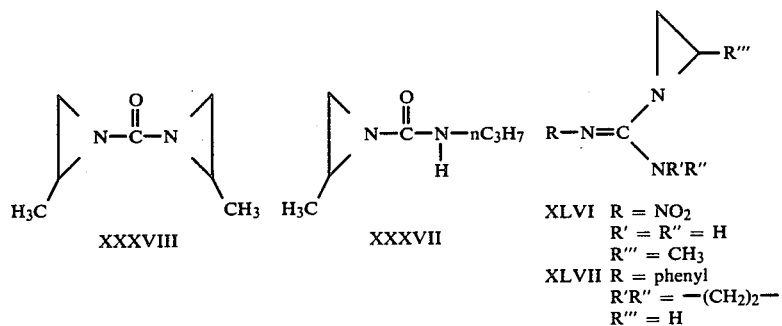
XLVI R = NO₂
R' = R'' = H
R''' = CH₃
XLVII R = phenyl
R'R'' = —(CH₂)₂—
R''' = H
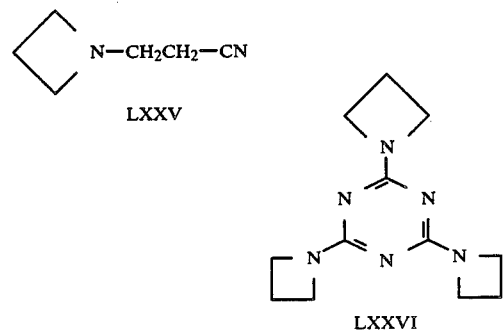
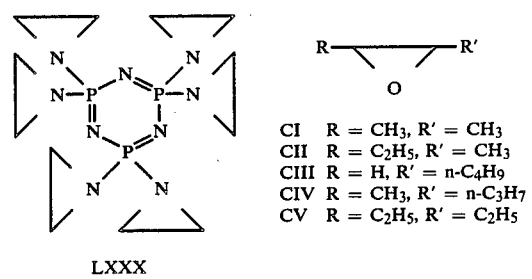
CI R = CH₃, R' = CH₃
CII R = C₂H₅, R' = CH₃
CIII R = H, R' = n-C₄H₉
CIV R = CH₃, R' = n-C₃H₇
CV R = C₂H₅, R' = C₂H₅
LXXX
CXX  R = R' = R'' = H
CXXI  R = H, R' = R'' = CH₃
CXXIII R = C₂H₅, R' = H, R'' = n-C₃H₇
CXXIV R = H, R' = CH₃, R'' = CH₂OH
CXXV  R = R' = H, R'' = OH
CXXII TABLE 3-continued

CXXVI

Reactions of Nitrogen Oxides with Heterocyclic compounds General Procedures

A. Reaction with $N_2O_5$

Where the heterocyclic compound consisted of an aziridine or azetidine, the heterocyclic compound (20 mmol) was dissolved in the appropriate dry inert solvent (10-15 ml) and added dropwise with stirring and cooling to a 4.4M solution of $N_2O_5$ in the same dry solvent (usually 20-40 ml) prepared by dissolving solid $N_2O_5$ (prepared by the method described previously) in the solvent. After addition was complete (usually 10-15 minutes) the mixture was stirred for a further 0.5-1 hour at the temperature of addition. Thereafter the mixture was allowed to warm to room temperature and stirred at this temperature for an additional period of 1-2 hours, or until completion of reaction was indicated (glc, tlc, hplc or $^1H$ nmr). The reaction was generally carried out at or below room temperature in order to minimise the thermal decomposition of $N_2O_5$ and in some cases to avoid losses of the reacting compound where it's volatility was high. Precautions were taken to avoid hydrolysis of the $N_2O_5$ by atmospheric water vapour. The reaction mixture was then drowned in ice-water and the organic layer separated. The aqueous layer was extracted with dichloromethane and the combined extracts were washed further with saturated sodium bicarbonate solution to remove any excess acidity, dried over anhydrous $MgSO_4$ and evaporated under water-pump vacuum below 30° C. The product, in the form of an oil or white solid was then identified by spectroscopy and, in a few cases, examined by glc or hplc to assess its purity.

Where the heterocyclic compound consisted of an epoxide (oxirane), a slightly different procedure was adopted reflecting the generally higher reactivity of epoxide groups towards $N_2O_5$. When the 4.4M solution of $N_2O_5$ was at the required temperature (usually 0° C.) sufficient of an organic solution of the epoxide (about 500 mg per ml) was added over 2 minutes to achieve the desired ratio of epoxide to $N_2O_5$ in the reaction mixture. The solution was then stirred for a further 5 minutes. No exotherms were observed. Anhydrous, moisture free conditions were maintained throughout. The solution was then agitated with saturated sodium carbonate solution to remove any excess acidity and the organic layer was separated, dried over anhydrous magnesium sulphate and filtered. The solvent was removed on a rotary evaporator at 30° C. under reduced pressure. The product was then examined as described previously.

B. Reaction with $N_2O_4$ and subsequent oxidation of the product

A solution of $N_2O_4$ was prepared by absorption of the gas into a dry inert solvent, and the hetercyclic compound in the same dry solvent was added slowly to this $N_2O_4$ solution with mixing until the desired molar ratio of reactants had been achieved. The reaction mixture was stirred for 30 minutes at the desired temperature ($-25°$ C. to 25° C.) and the resultant product was oxidised, in situ, with an anhydrous oxidising agent for example ozone. Anhydrous conditions were employed throughout. After removal of any excess acidity with soduim hydrogen carbonate solution, the product was isolated by vacuum distillation of the solvent.

SPECIFIC EXAMPLES

The structural formulae of the nitrated products of the following Examples are given in Table 4 below:

XVI

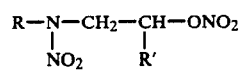

XX   R = $CH_2CH_2CN$, R' = $CH_3$
XXI  R = $CH_2CH_2CN$, R' = H
XXII R = n-$C_4H_9$, R' = H

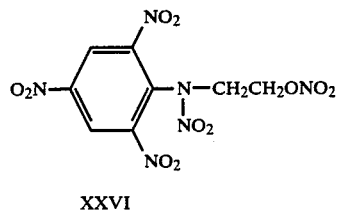

XXVI

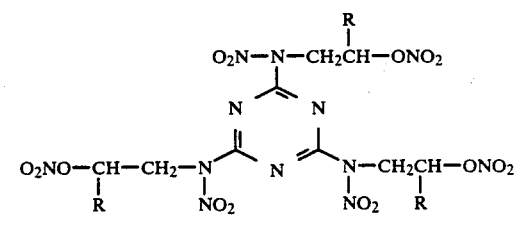

XXVII  R = H
XXVIII R = $CH_3$

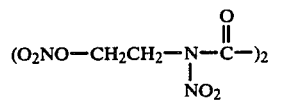 XXXII
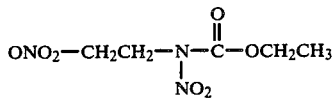 XXXIV
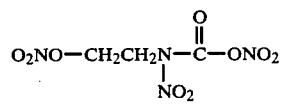 XXXV
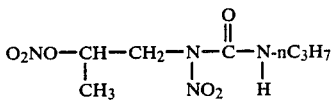 XXXIX
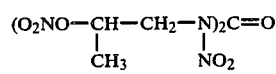 XLIII
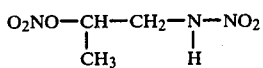 XLIV
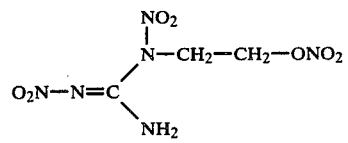 XLVIII
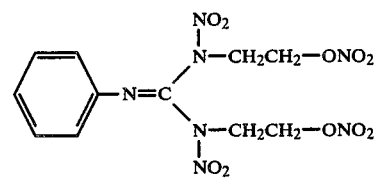 XLIX
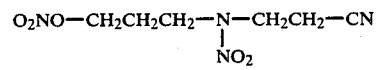 LXXVII
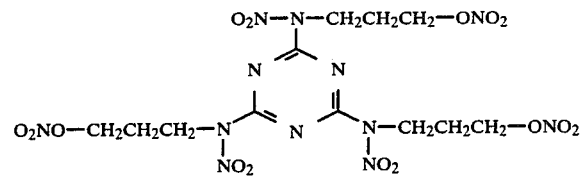 LXXVIII
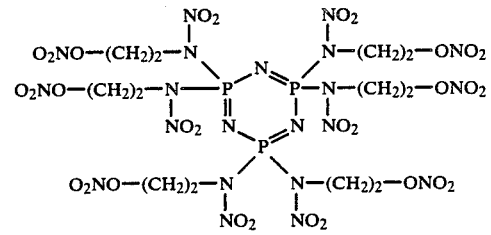 LXXXI

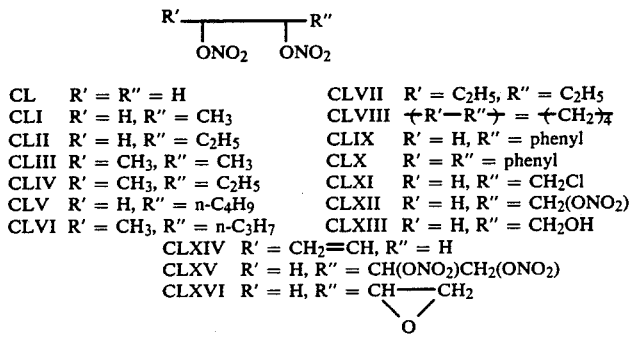

| | | | |
|---|---|---|---|
| CL | R' = R'' = H | CLVII | R' = C₂H₅, R'' = C₂H₅ |
| CLI | R' = H, R'' = CH₃ | CLVIII | $(R'-R'')$ = $(CH_2)_4$ |
| CLII | R' = H, R'' = C₂H₅ | CLIX | R' = H, R'' = phenyl |
| CLIII | R' = CH₃, R'' = CH₃ | CLX | R' = R'' = phenyl |
| CLIV | R' = CH₃, R'' = C₂H₅ | CLXI | R' = H, R'' = CH₂Cl |
| CLV | R' = H, R'' = n-C₄H₉ | CLXII | R' = H, R'' = CH₂(ONO₂) |
| CLVI | R' = CH₃, R'' = n-C₃H₇ | CLXIII | R' = H, R'' = CH₂OH |

CLXIV  R' = CH₂=CH, R'' = H
CLXV   R' = H, R'' = CH(ONO₂)CH₂(ONO₂)
CLXVI  R' = H, R'' = CH——CH₂
                          \O/

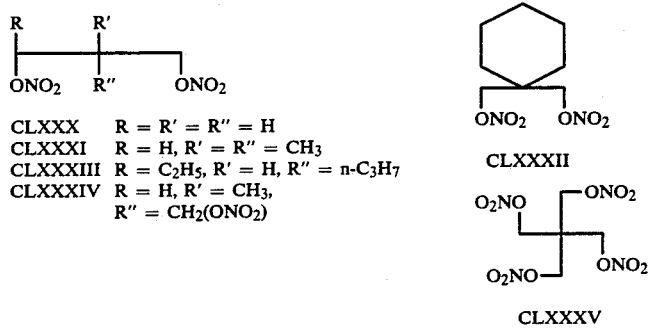

REACTION OF NITROGEN OXIDES WITH AZIRIDINES AND AZETIDINES

Details of quantities of reagent and conditions employed in each of the following Examples 1–16 are summarised in Table 5 below. Most of the products of the following Examples were characterised by their $^1$H nmr, $^{13}$C nmr, and ir spectral data, and some were further characterised by hplc, glc or tlc. The spectral data of these products is presented in Tables 6 to 8 below.

1(a) Propyleneimine (X)

A solution of propyleneimine (0.604 g, 10.5 mmol) in dichloromethane (10 ml) was added dropwise with stirring over 10 minutes to a solution of N₂O₅ (1.75 g, about 16 mmol) in the same solvent (25 ml) at 5° to 6° C. The mixture was stirred for 2.5 hours at room temperature. A pale yellow oil (0.70 g) separated out. The mixture was then worked up as follows. The dichloromethane layer was quenched in ice water, stirred for 1–2 hours, separated, dried (MgSO₄) and evapourated to give a very pale yellow oil (0.325 g, 18.5% yield) which was identified as propane-1,2-diol dinitrate from its spectra (ir and $^1$H nmr) by comparison with an authentic sample of the same nitrate.

1(b) 2-Aziridineethanol (XV)

2-Aziridineethanol was reacted with N₂O₅ using the general procedure (A) described above. The product speareated as a pale yellow oil, which was pipetted out of the reaction vessel and examined by hplc. The product was found to contain a small amount, less than 10% by weight, of N-nitrodiethanolamine dinitrate (XVI) by comparison (hplc) with an authentic sample prepared by the method of G F Wright et al (*Canad J Res* (1942) 26B p89).

2. N-(2-Cyanoethyl)-2-methylaziridine (XVII)

Compound XVII was reacted with N₂O₅ using the general procedure (A). The product, a white crystalline solid, was found to be the nitramine nitrate NCCH₂CH₂N(NO₂)CH₂CH(CH₃)ONO₂ (XX) whose identity was established from its ir, $^1$H, $^{13}$C and mass spectra. It was found to have a melting point of 85°–86° C.

3. N-(2-Cyanoethyl)-aziridine (XVIII)

Compound XVIII was reacted with N₂O₅ using the general procedure (A) described above, except that a further solvent removal step using acetone was employed to entrain residual dichloromethane, yielding a white fused solid, mpt 61° C. This product was identified as the nitramine nitrate NCCH₂CH₂N(NO₂)CH₂CH₂ONO₂ (XXI).

4. N-(n-Butyl)-aziridine (XIX)

Reaction of compound XIX with N₂O₅, general procedure (A), gave a nitramine nitrate identified as n-C₄H₉-N(NO₂)CH₂CH₂ONO₂ (XXII) in the form of an oil.

5. N-Picrylaziridine (XXIII)

Compound XXIII was reacted with N₂O₅ using the general procedure (A) described above. The product precipitated immediately as a yellow oil which crystallised on standing for about 30 minutes. The supernatant liquid was decanted and the product collected on a filter paper and washed with water. The product was identified from its spectra ($^1$Hnmr and ir) and by comparison (hplc and mixed MPT) with an authentic sample prepared by the method of L R Clark (*Ind Eng Chem* (1933) 25, p1385) as the tetryl derivative Pic-N(NO₂)CH₂CH₂ONO₂ (Pic=2,4,6 trinitrophenyl), labelled compound XXVI (also known as "Pentryl").

6. N,N,N',N',N'',N''-Triethylenemelamine (XXIV)

Compound XXIV was reacted with $N_2O_5$ using the general procedure (A) described above, except an additional step was involved consisting of treating the product by trituration with ethanol. The treated product formed a fine white solid which was recrystallised from ethanol-acetonitrile mixture, mpt 72°–73° C., and which was identified as a novel trialkyltrinitromelamine derivative $C_3N_3(N(NO_2)CH_2CH_2ONO_2)_3$ (XXVII).

7. N,N,N',N',N'',N''-Tripropylenemelamine (XXV)

Compound XXV was reacted with $N_2O_5$ using the general procedure (A) described above, except that an additional step was involved consisting of treating the product by trituration with methanol. The treated product formed a fine while solid, identified as a novel trialkyltrinitromelamine derivative $C_3N_3(N(NO_2)CH_2CH(CH_3)ONO_3)$ (XXVIII).

8. Diethyleneoxamide (XXXI)

1.25 mmol of the oxamide XXXI was dissolved in 6–7 ml of sulpholane (tetrahydrothiophene-S,S-dioxide) and added dropwise to 6–7 ml of a 4.4N solution of $N_2O_5$ in dichloromethane. After 30 minutes at low temperature the homogeneous mixture was allowed to warm to room temperature, then solid $NaHCO_3$ was added to neutralise excess $N_2O_5$. Examination of the solution by hplc (RP nitrile column, acetonitrite-water 4:1) indicated the known nitrate bis-(2-hydroxyethyl)-N,N'-dinitrooxamide dinitrate (NENO, XXXII) as the sole product by comparison with an authentic sample of NENO prepared by the method of G R Wright et al (*Canad J Res* (1948), 26B, 401).

9. Ethyl N,N-ethylenecarbamate (XXXIII)

Compound XXXIII was reacted with $N_2O_5$ using the general procedure (A) described above. The product was identified as ethyl-N-(2-hydroxyethyl)-N-nitrocarbamate (XXXIV) together with a small amount, detected by $^{13}C$ nmr and hplc, of the acyl nitrate XXXV. The proportion of compound XXXV in the product was found to increase with increasing $N_2O_5$ used in the reaction mixture, indicating that oxy-alkyl groups are generally susceptible to attack by $N_2O_5$.

10. N-Propyl-N,N'-propyleneurea (XXXVII)

Compound XXXVII was reacted with $N_2O_5$ using the general procedure (A) described above. A complex mixture of products was produced, one of which was identified as the nitramine nitrate (XXIX).

11. Dipropyleneurea (XXXVIII)

Compound XXXVIII was reacted with $N_2O_5$ using the general procedure (A) described above. The reaction took place smoothly to give the dinitrourea derivative XLIII. This derivative was found to hydrolyse readily to yield primary nitramines, e.g. compound XLIV.

12. N-Nitro-N',N'-propyleneguanidine (XLVI)

Compound XLVI was reacted with $N_2O_5$, general procedure (A), to produce a viscous oil which was insoluble in the reaction medium. Decantation of the solvent (in which no solute was found to remain) furnished a hygroscopic solid which was immediately characterised spectroscopically. The solid was found to consist of a mixture of compounds, one of which was identified as the known corresponding nitramine nitrate XLVIII.

13. N-Phenyl-N',N''-diethyleneguanidine (XLVII)

Compound XLVII was reacted with $N_2O_5$, general procedure (A), to produce a viscous red oil with the consistency of toffee which contained, from its hplc, no fewer than 10 components. One of these components was identified as the corresponding nitramine nitrate compound XLIX. Other components were identified as versions of compound XLIX in which the aryl group -Ph had undergone a degree of nitration.

14. N-(2-Cyanoethyl)-azetidine (LXXV)

Compound LXXV was reacted with $N_2O_5$, general procedure (A), to produce a mobile colourless oil identified as the nitramine nitrate $ONO_2CH_2CH_2CH_2N(NO_2)CH_2CH_2CN$ (LXXVII).

15. 2,4,6-Tris-(1-azetidinyl)-1,3,5-triazine (LXXVI)

Compound LXXVI was reacted with $N_2O_5$ in a similar manner to that described in Example 6 above, to produce a visious, semicrystalline glass identified as a novel trialkyltrinitromelamine derivative $C_3N_3(N(NO_2)CH_2CH_2CH_2ONO_2)_3$ (LXXVIII).

16. 2,2,4,4,6,6-Hexakis-(1'-aziridinyl)cyclotriphosphaza-1,3,5-triene (LXXX)

Compound LXXX was reacted with 6.6 mol $N_2O_5$ in $CDCl_3$ under conditions similar to those described under general procedure (A) (1.25 hr at 0° to 5° C.). The product separated as a fine white solid which was filtered off, washed with a little solvent and dried to give 2,2,4,4,6,6-hexakis-(2'-hydroxyethylnitramino)cyclotriphosphaza-1,3,5-triene hexanitrate (LXXXI) ("nitroapholate"), mpt 105° C. (dec.), yield 60%, which had i.r. and $^1H$ nmr spectra consistent with the proposed structure. The product LXXXI had a density (measured by flo tation) of 1.75 and an* F of I of 17 (ie more sensitive than HMX).

(*F of I = Figure of Insensitiveness)

TABLE 5

Reactions of N-Substituted Aziridines and Azetidines with $N_2O_5$

| Example | Substrate | Mol. ratio $N_2O_5$:substrate | Solvent | Temp. °C. | Principal Product | Yield % |
|---|---|---|---|---|---|---|
| 1(b) | XV | 2.5:1 | $CH_2Cl_2$ | −5 + 5 | XVI | ca 10* |
| 2 | XVII | 1.25:1 | $CH_2Cl_2$ | −10 to −5 | XX | 69.5 |
| 3 | XVIII | 1.1:1 | $CH_2Cl_2$ | −5 ± 5 | XXI | 56 |
| 4 | XIX | 1:1 | $CDCl_3$ | 0 ± 2 | XXII | 69 |
| 5 | XXIII | 1.13:1 | $CDCl_3$ | 0 ± 2 | XXVI | 76 |
| 6 | XXIV | 3.3:1 | $CH_2Cl_2$ | −5 ± 2 | XXVII | 95.5 |
| 7 | XXV | 3.3:1 | $CH_2Cl_2$ | −5 ± 2 | XXVIII | 77.5 |
| 8 | XXXI | 2.24:1 | $CH_2Cl_2$/sulpholane | −10 to −7 | XXXII | ca 80* |

TABLE 5-continued

Reactions of N-Substituted Aziridines and Azetidines with $N_2O_5$

| Example | Substrate | Mol. ratio $N_2O_5$:substrate | Solvent | Temp. °C. | Principal Product | Yield % |
|---|---|---|---|---|---|---|
| 9 | XXXIII | 1.1:1 | $CDCl_3$ | −5 to 0 | XXXIV | 81.5 |
| 9 | " | 1:1 | " | " | " | 67 |
| 10 | XXXVII | 1.3:1 | $CCl_4$ | −5 to 0 | XXXIX | ca 20* |
| 11 | XXXVIII | 2.2:1 | $CDCl_3$ | −10 to −5 | XLIII | 50 |
| 12 | XLVI | 1.28:1 | $CCl_4$ | −5 to 0 | XLVIII | ca 10* |
| 13 | XLVII | 2.2:1 | $CDCl_3$ | −5 + 5 | XLIX | ca 2–3* |
| 14 | LXXV | 1.16:1 | $CH_2Cl_2$ | −10 to +5 | LXXVII | 76.5 |
| 15 | LXXVI | 3.3:1 | $CH_2Cl_2$ | −5 | LXXVIII | 80 |
| 16 | LXXX | 6.6:1 | $CDCl_3$ | 0 to 5 | LXXXI | 60 |

Key to Abbreviations
*: Product not isolated as pure compound - identified by spectroscopy or by comparison with authentic sample.

TABLE 6

$^1$H Nmr Spectral Data

| Compound | Solvent | δ (ppm) |
|---|---|---|
| XVI | $CDCl_3$ | 4.15(t,4); 4.80(t,4) |
| XX | " | 1.35(d,3); 2.75(t,2); 3.5-4.5(m,4); 5.40(m,1) |
| XX | $D_6$-acetone | 1.40(d,3); 2.90(t,2); 4.2(m,4); 5.5(m,1) |
| XXI | $CDCl_3$ | 2.85(t,2); 4.12(m,4); 4.69(t,2) |
| XXI | $D_6$-acetone | 2.90(t,2); 4.23(m,4); 4.85(t,2) |
| XXII | $CDCl_3$ | 1.0(d,3); 1.1-1.85(m,4); 3.65-4.15(m,4); 4.80(t,2) |
| XXVI | $D_6$-acetone | 4.59(m,2); 4.90(m,2); 9.42(s,2) |
| XXVII | $CDCl_3$ | 4.83(brs) |
| XXVIII | " | 1.48(d,9); 4.60(m,6); 5.50(m,3) |
| XXXII | $D_6$-acetone | 4.82(m) |
| XXXIV | $CDCl_3$ | 1.37(t,3); 4.2-4.8(m,6) |
| XLIII* | " | 1.48(d,6); 4.42(m,4); 5.45(m,2) |
| XXXIX* | $CCl_4$ | 0.8-1.9(m,8); 4.0-4.4(m,4); 5.3(m,1) |
| XLVIII* | $CDCl_3$ | 1.5(d,3); 4.45(m,2); 5.50(m,1) |
| XLIX* | " | 3.8-4.9(m,8); 7.2-8.4(m,4) |
| LXXVII | $CDCl_3$ | 2.20 (qn,2); 2.90 (t,2); 4.05 (m,4); 4.62(t,2) |
| LXXVIII | $D_6$-acetone | 2.28 (m,6); 4.45 (m,12) |
| LXXXI | " | 4.3-5.0(m) |

TABLE 7

$^{13}$C Nmr Spectral Data $$\underset{7}{C}-\underset{6}{C}-\underset{5}{CH_2}-\underset{4}{CH_2}-\underset{}{N}-\underset{1}{CH_2}-\underset{2}{CH_2}-ONO_2 \text{ or}$$
with $NO_2$ on N $$\underset{6}{C}-\underset{5}{CH_2}-\underset{4}{CH_2}-\underset{}{N}-\underset{1}{CH_2}-\underset{2}{CH}-ONO_2$$
with $NO_2$ on N and $CH_3$ on C2

| Compound | C1 | C2 | C3 | C4 | C5 | C6 | C7 |
|---|---|---|---|---|---|---|---|
| XX | 54.88 | 79.04 | 15.88 | 49.19 | 16.25 | 118.26 | — |
| XXI | 50.20 | 70.50 | — | 49.19 | 16.09 | 118.32 | — |
| XXII | 52.57 | 68.98 | — | 48.78 | 28.35 | 19.63 | 19.63 |
| XVI | 50.39 | 70.54 | — | — | — | — | — |

$$\underset{U}{\overset{C-C-V}{\diagdown}}\underset{4}{C}-N-\underset{1}{CH_2}\underset{2}{CH_2}ONO_2 \text{ or}$$
with $NO_2$ on N $$\underset{U}{\overset{W}{\diagdown}}\underset{4}{C}-N-\underset{1}{CH_2}\underset{2}{CH}-ONO_2$$
with $NO_2$ on N and $CH_3$ on C2

| Compound | C1 | C2 | C3 | C4 | C5 | C6 | C7 |
|---|---|---|---|---|---|---|---|
| XXVII | | | | | | | |
| XXVIII | 51.54 | 77.49 | 15.84 | 165.03 | — | — | |
| XXXIV | 46.23 | 68.76 | — | 149.70 | 65.13 | 13.56 | |
| XLIII | 51.16 | 76.73 | 16.00 | 147.75 | — | — | |
| XXXIX | 48.02? | 77.38? | 16.00 | u/a | u/a | u/a | |

TABLE 8

IR Spectral Data

| Compound | Liq .film (L) or mull (M) | $\nu_{max}$ (cm$^{-1}$) >N—NO$_2$as | —ONO$_2$as | >N—NO$_2$s/ —ONO$_2$s | Other |
|---|---|---|---|---|---|
| XX | M | 1523 | 1636 | 1285/1277 | 2250(C≡N) |
| XXI | M | 1519 | 1632 | 1277/1270 | 2249(C≡N) |
| XXII | L | 1515 | 1639 | 1288/1273 | |
| XXVI | M | 1572 | 1639 | 1277 | 1547, 1340(NO$_2$) |
| XXVII | L | 1548 | 1644 | 1280 | |
| " | M | 1552 | 1630 | 1280/1269/1244 | |
| XXVIII | L | 1550 | 1637 | 1277 | |
| XXXII | M | 1587 | 1637 | 1278/1257 | 1736, 1710(C=O) |
| XXXIV | L | 1581 | 1642 | 1278 | 1777, 1742(C=O) |
| XLIII | L | 1600 | 1639 | 1288/1277 | 1723(C=O) |
| XXXIX | L | 1594 | 1633 | 1283 | 3392(N—H), 1719 (C=O), 1511 (u/a), 1385(u/a) |
| XLVIII | L | 1577/1532 | 1632 | 1288/1277 | ? (NO$_2$) |
| XLIX | (CDCl$_3$ soln) | 1589 | 1650 | 1277 | 1524, 1344 (NO$_2$) |
| XVI | M | 1523 | 1638 | 1283 | |
| LXXVII | L | 1521 | 1631 | 1280 | |
| LXXVIII | L | 1548 | 1630 | 1280 | |
| LXXXI | L | 1581 | 1633 | 1279 | 1214 (P—N ring) |

| Key to Abbreviations in Spectral Tables 6 to 8 | | | |
|---|---|---|---|
| $^1$H NMR | | | |
| s = singlet | qn = quintet | | *Spectrum contained other |
| d = doublet | m = multiplet | | peaks due to impurities |
| t = triplet | brs = broad singlet | | (not listed). |
| qr = quartet | | | |

Integrated intensities are shown in parentheses after the multiplicities.

$^{13}$C NMR

All spectra were recorded in CDCl$_3$.
U = O; V = O or NH; W = CON(NO$_2$)CH$_2$CH(CH$_3$)ONO$_2$.

IR s = symmetrical group absorption
as = asymmetrical group absorption
Only $\nu_{max}$ (NO$_2$) and other diagnostically useful bands reported.

REACTION OF NITROGEN OXIDES WITH EPOXIDES

In the following Examples, the general reaction conditions employed for a number of specified epoxides are given. More detailed reaction conditions and product yields are given in Tables 9(a) and 9(b) below. Characterisations of some of the products of these reactions are given in Table 10 below.

17. Ethylene Oxide (a) Reaction with N$_2$O$_5$

Ethylene oxide was reacted with N$_2$O$_5$ using the general procedure (A) described above. The product was the dinitrate ester of ethylene glycol (CL), yield 98%. In some runs small amounts of ethylene glycol mononitrate were observed through the reaction of traces of nitric acid with ethylene oxide.

(b) Reaction with N$_2$O$_4$ and an oxidising agent

Ethylene oxide was reacted with N$_2$O$_4$, general procedure (B) above except that the subsequent oxidation step was omitted, in various solvents and at various reactant ratios and temperatures. The conditions employed are summarised in Table 9(a) below. Virtually the sole product of these reactions, confirmed by IR and $^1$H nmr spectroscopy, was ethylene glycol mononitrate (EGMN) produced by the hydrolysis during the recovery procedure of the unstable vicinal nitrite-nitrate ester O$_2$NO—CH$_2$—CH$_2$—ONO. Traces of diethylene glycol mononitrate were also detected in some cases. The slow addition of epoxide to N$_2$O$_4$, the rather than addition of N$_2$O$_4$ to epoxide, was found to suppress formation of unwanted dimer and oligomer contaminants of formula O$_2$N—(CH$_2$—CH$_2$—O)$_n$—CH$_2$—CH$_2$—ONO in the reaction mixture prior to recovery (n>1).

Ethylene oxide was also reacted with N$_2$O$_4$ in the gas phase (ie in the absence of solvent). The conditions employed are also summarised in Table 9(a).

The experimental run employing dichloromethane solvent, a 1:1 epoxide to N$_2$O$_4$ mol ratio and a reaction temperature of 0° C. was repeated except that on this occasion the subsequent oxidation step was employed. When excess ozone was employed, oxidation proceeded very smoothly and virtually quantitative conversion of the unstable nitrite-nitrate to ethylene glycol dinitrate EGDN (CL) in 98% yield (based on EGMN) was achieved with no evidence of any side reaction. The product was therefore virtually uncontaminated, providing a facile and clean route to this product. When excess homogeneous organic oxidant (m-chloroperbenzoic acid MCPBA) was employed, EGDN was still generated in significant quantities (about 70% yield). However, the product was found to be contaminated with m-chlorobenzoic acid, unchange MCPBA and, possibly, the products of side reactions all of which were difficult to separate from EGDN.

18. Propylene Oxide

Propylene oxide was reacted with N$_2$O$_5$, general procedure (A), to give propane-1,2-diol dinitrate (CLI) in 98% yield. The isolated material showed a single peak on glc analysis with a retention time corresponding to that of an authentic sample prepared by mixed acid nitration of propane-1,2-diol. Both ir and $^1$H nmr analysis confirmed the structure, and the physical properties agreed with published data for this known compound.

19. n-But-1-and n-But-2-ene oxides n-But-2-ene oxide (CI) was prepared from n-but-2-ene, whereas a commercial sample of n-but-1-ene oxide was used. Both the 1-and 2-ene oxides gave very high isolated yields (98% and 97% respectively) of the corresponding vicinal dinitrate esters CLII (butane-1,2-diol dinitrate) and CLIII (butane-2,3-diol dinitrate) when reacted with N$_2$O$_5$ using general procedure (A). GLc analysis of both products gave single peaks and the retention times were identical with those obtained with the products of mixed-acid nitration of the corresponding diols. Spectroscopic analysis of, and physical data on these materials were compared with those of authentic samples and with published values, and confirmed both their structures and purity.

20. n-Pent-2-ene Oxide (CII)

n-Pent-2-ene oxide, prepared from pent-2-ene (cis/trans) reacted rapidly with N$_2$O$_5$ (no epoxy signals visible in $^1$H nmr spectra after 10 min at 5° C.) using general procedure (A) to give the expected product, pentane-2,3-diol dinitrate (CLIV), in 90% yield. This material showed the predicted $^1$H nmr and ir spectra, and gave a single peak on glc analysis.

21. n-Hex-1-(CIII), n-Hex-2-(CIV), and n-Hex-3-(CV) ene oxides

All three positional isomers of n-hexene oxide were prepared from the corresponding hexenes. Reaction with N$_2$O$_5$, general procedure (A), occurred rapidly in all cases, and yields in excess of 90% of the corresponding vicinal dinitrates esters CLV, CLVI and CLVII were obtained. Chromatographic and spectroscopic data were compared with those of authentic samples prepared by mixed-acid nitration of the corresponding diols and were found to be identical, as were the physical data.

22. Cyclohexene Oxide

The reaction of cyclohexene oxide with N$_2$O$_5$ general procedure (A), was found to be essentially quantitative, producing cyclohexane-1,2-diol dinitrate (CLVIII) with no detectable impurities. Again an authentic sample of the vicinal dinitrate was prepared by conventional nitration of the 1,2-diol and was used to confirm the identity of the product.

23. Styrene Oxide

Reaction of styrene oxide with N$_2$O$_5$, general procedure (A), resulted in the exclusive formation of 1-phenylethane-1,2-diol dinitrate (CLIX). Since there are no published data on this material, it was identified by analysis of its $^1$H nmr and ir spectra. It was shown to be pure by the appearance of a sharp single peak on the glc trace.

24. Stilbene Oxide

The product of reaction of stilbene oxide with $N_2O_5$ using general procedure (A) gave a narrow single peak on glc analysis, and $^1$H nmr analysis indicated that it was the expected 1,2-diphenylethane-1,2-diol dinitrate (CLX). No published data on this compound were found. Isolated yield was >95%.

25. Epichlorohydrin

The reaction of $N_2O_5$ with epichlorohydrin general procedure (A), proceeded rapidly and cleanly to yield a single product as evidenced by glc. This was identified as 3-chloropropane-1,2-diol dinitrate (CLXI) by H$^1$ nmr and by comparison with an authentic sample prepared by conventional mixed acid nitration of the parent diol.

26. Glycidol

Since glycidol possesses an hydroxyl ligand in addition to the epoxide, by the following equation total nitration of the compound required a minimun of 2:1 stoichiometry on the assumption that the nitric

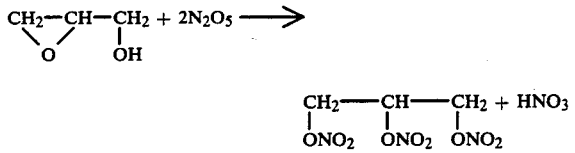

acid generated does not participate in the reaction. The product of this total nitration reaction is nitroglycerine (NG) (CLCXII)

Under these stoichiometric conditions the reaction with $N_2O_5$ was found to proceed rapidly and smoothly using general procedure (A), to give NG quantitatively, the product being identified by reference to an authentic sample.

When the reaction was carried out at equimolar stoichiometry a single product was obtained in very high yield (92%). This was identified as glycerol-1,2-dinitrate (CLXIII) by $^1$H nmr and by comparison with an authentic sample. In this case, however, general procedure (A) was modified to the extent that the normal order of mixing the reagents was reversed and the $N_2O_5$ solution was added to the glycidol solution in order to ensure that the epoxide was present in excess at all time.

27. Butadiene monoepoxide

Butadiene nomoepoxide was reacted with $N_2O_5$ as described above in general procedure (A). The product was 3,4-butenediol dinitrate (CLXIV)

28. Butadiene Diepoxide (a) Butadiene diepoxide, being a difunctional species, was reacted with $N_2O_5$ at a stoichiometry of 1:2 using general procedure (A). Reaction was rapid and smooth, and a single product resulted as indicated by glc in very high yield. The material was identified by $^1$H nmr and ir examination as erythritol tetranitrate (CLXV). Its physical properties were compared with published data.

A similar reaction was then carried out in which equimolar amounts of butadiene diepoxide and $N_2O_5$ were reacted together using general procedure (A), except that the nitrogen oxide was added to the epoxide. Again, reaction was rapid and smooth and a single product was produced (glc) in high yield. $^1$H nmr and ir analysis showed this compound to be 1,2-epoxybutane-3,4-diol dinitrate (CLXVI).

29. Epoxidised HTPB

Samples of each of the epoxidised HTPB's prepared as described above were reacted with $N_2O_5$ using the following procedures:

(a) Product Preparation without removal of unreacted epoxide groups 50 g Epoxidised HTPB was dissolved in 200 ml dichloromethane in a dry three-necked round-bottom flask fitted with a thermometer, stirrer and calcium chloride guard tube. The flask was then immersed in an acetone/solid $CO_2$ bath maintained at $-10°$ C. The calculated amount of $N_2O_5$ required for complete equimolar reaction with the epoxide groups (18.9 g if HTPB is exactly 20% epoxidised) was dissolved in 100 ml dichloromethane and this was added slowly to the reaction vessel under moisture-free conditions.

After addition was complete the cold bath was removed and the reaction vessel allowed to warm to room temperature. Excess sodium bicarbonate in aqueous solution was then stirred with the reaction mixture for 20 minutes to remove any acidity, and the solution filtered. The nitrated polymer was subsequently isolated by stripping off the solvent on a rotary evaporator at 40° C. The last traces of solvent were removed by keeping the polymer in a vacuum oven at 25° C. for a minimum period of 24 hours. Although the product is susceptible to aerial oxidation, it can be stored in a stoppered container at $-20°$ C. for long period (months) without significant deterioration. The product materials were all liquid rubbers.

A product prepared by this procedure from a 20% epoxidised HTPB was found to contain a residual epoxide level of about 4% of the double bonds present in the initial HTPB prior to expoxidation, because some of the $N_2O_5$ had reacted with double bonds on the HTPB backbone by the following equation:

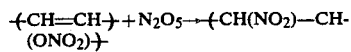

This meant that the product was empirically equivalent to nitrated HTPB containing about 18% vicinal di (nitrate ester) $-\!\!+\!CH(ONO_2)$ $CH(ONO_2)+\!\!-$ groups, about 2% vicinal C-nitro-C-nitrate ester $-\!\!+\!CH(NO_2)$ $CH(ONO_2)+\!\!-$ groups and about 4% epoxide groups (all percentages relate to the number of double bonds in the initial HTPB, and two functional groups replace the destruction of one double bond). It was assumed that the (—OH) terminal groups remained unreacted because the liquid product was subsequently successfully reacted with isophorone diisocyanate (see Example 29(d) below).

(b) Product Preparation by reaction with excess $N_2O_5$

The procedure of Example 29a was repeated, except that the calculated amount of $N_2O_5$ used was 1.5 times that required for complete equimolar reaction with all epoxide and double bonds in the epoxidised HTPB, yielding highly nitrated polymers containing about x% vicinal di (nitrate ester) groups and (100−x)% vicinal C-nitro-C-nitrate ester groups where x is the percentage degree of initial HTPB epoxidation. The presence of remaining —OH groups in the products was not investigated.

(c) Product Preparation with removal of unreacted epoxide groups

Analysis of the nitrated polymer showed that invariably there were epoxide groups remaining after the $N_2O_5$ reaction the level being dependent on the reagent stoichiometry employed in the nitration process. Since such groups might interfere with the use of the product in some potential technological application, it was felt desirable to devise a technique to destroy the residual epoxide groups without affecting the polymer in any other way.

It was shown experimentally that reaction of the polymer with controlled amounts of nitric acid was ineffective in this regard, and the following method is recommended if epoxide removal is required; the procedure converts the unreacted epoxide groups to vicinal hydroxy-nitrates by the following equation:

Before addition of sodium bicarbonate described under Example a. above, a small sample of the solution was taken, neutralised and the solvent removed. The epoxide content was determined by the method of RR Jay (Analyt. Chem. (1964), 36, 667 and the amount of nitric acid equimolar to the residual epoxide in the remaining bulk solution calculated. A 10% excess of this value was then introduced as 70% nitric acid to the reaction mixture and the whole stirred for 10 minutes. The reaction conditions were such that the double bonds in the nitrated HTPB remained intact. The solution was then neutralised and the liquid product isolated as described under Example 29a. A product prepared from a 20% epoxidised HTPB by this procedure was found to contain a residual epoxide level of less than 0.1% of the number of double bonds in the initial HTPB.

The product therefore contained, on average (assuming the HTPB has about 50 butadiene units per chain), an additional two hydroxyl groups per chain so that its —OH functionality was about twice that of the initial HTPB (average functionality: 2.2). This increased functionality was reflected in an increased viscosity in this product over that produced from 20% epoxidised HTPB by the method of Example 29a.

d. Isocyanate cure of nitrated HTPB

Comparative experiments were carried out with HTPB and with the 20% nitrated product of Example 19a to determine the applicability of the isocyanate cure procedures, normal for HTPB in rubbery propellant technology, to nominally 20% nitrated HTPB prepared from 20% epoxided HTPB. The following experimental method was therefore applied to both materials to find out the parametric values which produced acceptable polyurethane rubbers.

The liquid polymer was preheated to 60° C. and then hand-blended, using a spatula, with isophorone diisocyanate (IPDI). The mixture was degassed under vacuum and poured into a PTFE mould of dimensions 25 mm×50 mm×2 mm. The filled mould was then heated in an oven at 90° C. for 18 hours before the resulting elastomer was removed and examined. The experiment was repeated for different relative concentrations of IPDI.

The optimum equivalence ratio (OH/NCO) for HTPB was found to be 1.0 (for an OH content of 0.7 m.equiv/g). Ratios significantly above or below this value yielded rubbers which were decidedly sticky, in contrast to the acceptable product obtained at equimolarity. On the admittedly questionable assumption that the OH content of the rubber remained unchanged on nitration, apart from the weight increase, the same observations were observed with the nitrated material at the same equivalence ratios. It may be assumed, therefore, that 20% nitrated HTPB may be efficiently cured with IPDI under the conditions obtaining for unmodified HTPB.

The properties of optimised IPDI-cured 20% nitrated HTPB were as follows:

Glass Transition Temperature (Tg): −31° C.
Heat of decomposition H: 260 cal/g
Autoignition Temperature: 155° C.
Heat of combustion: 9030 cal/g These properties (especially the low Tg value) indicate that this cured product would be suitable as a binding material in a solid rocket propellant. Since rubbery binder in rocket propellants should ideally have a Tg of not more than about −30° C., the degree of HTPB nitration should preferably not exceed about 25% of its original double bonds in total.

TABLE 9(a)

| Reactions of Ethylene Oxide with $N_2O_4$ | | | |
|---|---|---|---|
| Mol. Ratio $N_2O_4$:epoxide | Solvent | Temperature °C. | Product |
| 1:1 | $CH_2Cl_2$ | 0 | EGMN |
| 2:1 | " | 0 | (90%) |
| 1:1 | " | −25 | with |
| 1:1 | " | 25 | traces |
| 1:1 | $CH.Cl_3$ | 0 | of |
| 1:1 | $CCl_4$ | 0 | DEGMN |
| 1:1 | ether | 0 | |
| 1:1 | n—$C_6H_{14}$ | 0 | |
| 1:1 | none | 0 | |
| 1:1 | (gas phase) | 25 | EGMN only |
| 1:1 | (gas phase) | 100 | |
| 1:1 | (gas phase) | 150 | |

Key
EGMN = ethylene glycol mononitrate
DE = diethylene glycol mononitrate

TABLE 9(b)

| | | Reactions of Epoxides with $N_2O_5$ | | | | |
|---|---|---|---|---|---|---|
| Example | Substrate | $N_2O_5$:substrate | Total Solvent Volume (ml) | Reaction Temp (°C.)/Time (mins) | Principal Product | Isolated Yield (% of theoretic) | Purity (% by glc) |
| 17 | Ethylene oxide | 1.1:1 | 50 | 10−15/5 | CL | 98 | 100 |
| 18 | Propylene oxide | 1.1:1 | 50 | 10−15/5 | CLI | 98 | 100 |

TABLE 9(b)-continued
Reactions of Epoxides with $N_2O_5$

| Example | Substrate | $N_2O_5$:substrate | Total Solvent Volume (ml) | Reaction Temp (°C)/Time (mins) | Principal Product | Isolated Yield (% of theoretic) | Purity (% by glc) |
|---|---|---|---|---|---|---|---|
| 19 | n-But-1-ene oxide | 1.1:1 | 50 | 15–20/5 | CLII | 98 | 100 |
|  | CI | 1.1:1 | 50 | 15–20/5 | CLIII | 96 | 100 |
| 20 | CII | 1.1:1 | 40 | 0–5/15 | CLIV | 90 | 98+ |
| 21 | CIII | 1.1:1 | 40 | 15–20/5 | CLV | 95 | 99+ |
|  | CIV | 1.1:1 | 30 | 15–20/5 | CLVI | 98 | 100 |
|  | CV | 1.1:1 | 25 | 15–20/5 | CLVII | 93 | 99+ |
| 22 | Cyclohexene oxide | 1.1:1 | 50 | 15–20/5 | CLVIII | 99+ | 100 |
| 23 | Styrene Oxide | 1.1:1 | 50 | 15–20/5 | CLIX | 98 | 100 |
| 24 | Stilbene Oxide | 1.1:1 | 50 | 15–20/5 | CLX | 96 | 100 |
| 25 | Epichlorohydrin | 1.1:1 | 50 | 15–20/5 | CLXI | 92 | 100 |
| 26 | Glycidol | 2.1:1 | 100 | 0–10/10 | CLXII | 97 | 100 |
|  | Glycidol | 1:1 | 50 | 0–10/5 | CLXIII | 92 | 100 |
| 27 | Butadiene Monoepoxide | 1.1:1 |  |  | CLXIV |  |  |
| 28 | Butadiene Diepoxide | 2.1:1 | 100 | 0–10/10 | CLXV | 94 | 99 |
|  | Butadiene Diepoxide | 1:1 | 100 | 0–10/10 | CLXVI | 90 | 99 |

Note:
The solvent used in every example was dichloromethane

TABLE 10
Characterisation of nitrates prepared from epoxides

(A) NITROGLYCERINE

|  | Prepared by Method of Example 26 | Prepared by Conventional mixed acid nitration |
|---|---|---|
| R.I. ($n_D^{20}$) | 1.472 | 1.472 |
| Density (g.cc$^{-1}$ at 20° C.) | 1.593 | 1.592 |
| ir data |  |  |
| liquid film (cm$^{-1}$) | 1640<br>1270 | 1640<br>1270 |
| nmr data |  |  |
| d (ppm) | 4.9 (d,4)<br>5.8 (m,1) | 4.9 (d,4)<br>5.8 (m,1) |

(B) GLYCEROL - 1,2 - DINITRATE

|  | Prepared by Method of Example 26 | Prepared by Conventional mixed acid nitration |
|---|---|---|
| R.I. ($n_D^{20}$) | 1.463 | 1.463 |
| Density (g.cc$^{-1}$ at 20° C.) | 1.465 | 1.465 |
| ir data |  |  |
| liquid film (cm$^{-1}$) | 3400<br>1640<br>1265 | 3400<br>1640<br>1265 |
| nmr data |  |  |
| d (ppm) | 2.1 (m,2)<br>3.7 (brs,1)*<br>4.6 (d,2<br>5.4 (m,1) | 2.1 (m,2)<br>3.7 (brs,1)*<br>4.6 (d,2)<br>5.4 (m,1) |

(C) 3-CHLOROPROPANE-1,2-DIOL DINITRATE

|  | Prepared by Method of Example 25 | Prepared by Conventional mixed acid nitration |
|---|---|---|
| R.I. ($n_D^{20}$) | 1.458 | 1.458 |
| Density (g.cc$^{-1}$ at 20° C.) | 1.532 | 1.532 |
| ir data |  |  |
| liquid film (cm$^{-1}$) | 1640<br>1270<br>720 | 1640<br>1270<br>720 |
| nmr data |  |  |
| d (ppm) | 4.2 (d,2)<br>5.1 (qr,1)<br>5.8 (m,2) | 4.2 (d,2)<br>5.1 (qr,1)<br>5.8 (m,2) |

(D) PROPANE-1,2-DIOL DINITRATE

|  | Prepared by Method of Example 18 | Prepared by Conventional mixed acid nitration |
|---|---|---|
| R.I. ($n_D^{20}$) | 1.427 | 1.427 |
| Density (g.cc$^{-1}$ at 20° C.) | 1.377 | 1.377 |
| ir data |  |  |
| liquid film (cm$^{-1}$) | 1640<br>1260 | 1640<br>1260 |
| nmr data |  |  |
| d (ppm) | 1.8 (d,3)<br>4.7 (m,2)<br>5.4 (m,1) | 1.8 (d,3)<br>4.7 (m,2)<br>5.4 (m,1) |

REACTION OF NITROGEN OXIDES WITH OXETANES

In the following Examples, the reaction of $N_2O_5$ with various oxetanes is described which generally follow procedure (A) though with certain modifications. More detailed reaction conditions and product yields are given in Table 11 below. Characterisations of the products of these reactions are given in Tables 12 and 13 below.

30. Oxetane (CXX)

A solution of oxetane (0.90 g, 15.5 mmol) in $CH_2Cl_2$ (10 ml) was added dropwise over 25 minutes with stirring at 5°–10° C. (ice-bath) to a solution of $N_2O_5$ (2.17 g, ca 20 mmol) in $CH_2Cl_2$ (30 ml). The mixture was stirred for 45 min. at 10° C., then poured into ice-water, shaken, the organic layer extracted, washed with dilute NaHCO$_3$ solution and dried over MgSO$_4$. Removal of the solvent gave propane-1,3-diol dinitrate (CLXXX) as a colourless oil (2.26 g, 88%), identified by its $^1$H nmr and i.r. spectra, and by glc comparison with an authentic sample. This material had > 95% purity ($^1$H nmr).

31. 3,3-Dimethyloxetane (CXX1)

A solution of this oxetane (1.29 g, 15 mmol) in CH$_2$Cl$_2$ was treated with N$_2$O$_5$ (20 mmol) by the method of Example 30, except that the temperature was not allowed to exceed 15° C., and stirring was continued for a further 3 hours. After workup, 2,2-dimethylpropane-1,3-diol dinitrate (CLXXXI) was obtained as a colourless oil (2.12 g, 73%), identified by its $^1$H nmr and i.r. spectra. Comparison of the glc of this product with that of an authentic sample prepared by mixed acid nitration of an appropriate diol indicated the presence of impurities of longer retention time (presumably oligomeric) in addition to the dinitrate. The purity of the product of this Example was estimated to be 65–70% by comparison with an authentic sample.

32. 3,3-(Pentamethylene)-oxetane (CXXII)

This oxetane (10 mmol) was treated with N$_2$O$_5$ by the same method used in Example 31. After workup, the product was identified as 2,2-(pentamethylene)-propane-1,3-diol dinitrate (CLXXXII) (2.01 g, 86%) by comparison of its spectra ($^1$H nmr and i.r.) and glc with authentic material. The glc indicated that it was ca 75% pure, with material presumed to be oligomers accounting for the rest of the product.

33. 2-Propyl-3-ethyloxetane (CXXIII)

A solution of this oxetane (0.50 g, 0.4 mmol) in CDCl$_3$ (7–8 ml) was added dropwise over 5 minutes to a solution of N$_2$O$_5$ (0.60 g, 5.5 mmol) in the same solvent (15 ml), keeping the temperature below −5° C. The mixture was stirred for 10 min. at −5 to 0° C., then a sample was withdrawn for analysis by $^1$H nmr. The nmr spectrum indicated that the oxetane ring had been cleaved (rearrangement of midfield signals between δ 4 and δ 5 ppm), with the appearance of a new mid-field doublet (δ 4.46 ppm), all consistent with the production of the expected dinitrate (CLXXXIII). Stirring was continued for 1 hr at 0° to 5° C., then the mixture was worked up as described in Example 30 to give 0.41 g of a pale yellow oil identified as 2-ethylhexane-1,3-diol dinitrate (CLXXXIII) from its $^1$H nmr and i.r. spectra. The purity was found to be 46.5%, and the true yield of the dinitrate was 0.191 g (21%).

The product was judged to be impure by comparison of the i.r. and $^1$H nmr spectra with those of an authentic sample: additional moderate to weak absorptions at 1777, 1723, 1554 amd 1170 cm$^{-1}$ were present in the i.r., while the $^1$H nmr spectrum showed a weak downfield singlet (δ 11.3 ppm) assigned to carboxylate proton. These observations were consistent with contamination of the nitrate ester by small amounts of carboxylic compounds arising from oxidative side-reaction. The purity was assessed quantitatively by hplc vs an authentic sample using di-(n-butyl)phthalate as an internal standard.

34. 3-Methyl-3-(Hydroxymethyl) oxetane (CXXIV)

This oxetane (4 mmol) in CH$_2$CL$_2$ was added dropwise over 8 minute at −10° C. to N$_2$O$_5$ (15.7 mmol) in the same solvent (25 ml). The mixture, which had not shown any noticeable temperature change during the addition, was stirred whilst allowing to warm to 0°–5° C. over 30 minutes. The mixture was kept at this temperature with stirring for a further 15 hours. After a total of 28 hours, the mixture was worked up by the method described under Example 30 to give metriol trinitrate MTN (CLXXXIV) (0.90 g, 88% yield) which had i.r. and $^1$H nmr spectra identical to authentic material. No contaminants were detected in the end product.

By analogy with Examples 30–34 above, the following commercial important materials may be prepared using general procedure (A) or similar:

(1) Nitroglycerine (CLXII) from 3-hydroxyoxetane (CXXV) employing a molar ratio of N$_2$O$_5$ to (CXXV) of at least 2:1.
(2) Pentaerythritol tetranitrate PETN (CLXXXV) from spirocyclic bioxetane (CXXVI) employing a molar rate of N$_2$O$_5$ to (CXXVI) of at least 2:1.

TABLE 11
Reactions of Oxetanes with N$_2$O$_5$

| Example | Oxetane | Mol N$_2$O$_5$ Substrate | Solvent | Reaction Temp °C. | Reaction time (hr) | Principal Product | Yield % | Purity % |
|---|---|---|---|---|---|---|---|---|
| 30 | CXX | 1.33:1 | CH$_2$Cl$_2$ | 5 to 10 | 0.75 | CLXXX | 88 | >95 |
| 31 | CXXI | " | " | 10 to 15 | 3 | CLXXXI | 73 | 65–70 |
| 32 | CXXII | " | " | " | " | CLXXXII | 86 | ca 75 |
| 33 | CXXIII | 1.37:1 | CDCL$_3$ | −5 to +5 | 1.5 | CLXXXIII | 21 | * |
| 34 | CXXIV | 4:1 | CH$_2$Cl$_2$ | −10 to 15 | 28 | CLXXXIV | 88 | >95 |

Key
*Yields measured chromatographically vs standards of pure compounds.

TABLE 12
$^1$H Nmr Spectral Data

| Compound | (ppm) |
|---|---|
| CLXXX | 2.22(qn,2);4,65(t,4) |
| CLXXXI | 1.10 (s,6);4.28(s,4) |
| CLXXXII | 1.53(brs,10); 4.43(s,4) |
| CLXXXXIII | 0.8–1.75(m,12);1.8–2.2(m,1);4.46(d,2);5.20(qr,1) |
| CLXXXIV (in CDCL$_6$) | 1.20(s,3);4.50(s,6) |

TABLE 13
I.r. Spectral Data

| Compound | $v_{max}$ (cm$^{-1}$) —ONO$_2$as | —ONO$_2$s | —ONO$_2$gp | Other |
|---|---|---|---|---|
| CLXXX | 1633 | 1281 | 866 | — |
| CLXXXI | 1636 | 1278 | 866 | — |
| CLXXXII | 1635 | 1274/1284 | 866 | — |
| CLXXXIII | 1647/1631 | 1281 | 872/865 | — |
| CLXXXIV | (1659/1646/1627) | 1277 | 880 | — |

Key to Abbreviations in Spectral Tables 12 and 13

$^1$H NMR

| | | |
|---|---|---|
| s = singlet | qn = quintet | All spectra were run using |
| d = doublet | m = multiplet | CDCl$_3$ as solvent unless |
| t = triplet | brs = broad singlet | otherwise stated. |
| qr = quartet | | |

Key to Abbreviations in Spectral Tables 12 and 13

Integrated intensities are shown in parentheses after the multiplicities.

$^{13}$C NMR

All spectra were recorded in CDCl$_3$.

IR
- s = symmetrical group absorption
- as = asymmetrical group absorption
- u/a = band unassigned Only $\nu_{max}$ (NO$_2$) and other diagnostically useful bands are reported.

We claim:

1. A process for the production of a high energy material comprising the following steps:
   (a) reacting a heterocyclic strained ring compound, selected from the group consisting of oxiranes, oxetanes, aziridines and azetidines, with a nitrogen oxide selected from the group consisting of dinitrogen tetroxide (N$_2$O$_4$) and dinitrogen pentoxide (N$_2$O$_5$) to open said heterocyclic strained ring and afford, when the nitrogen oxide is N$_2$O$_4$, a product A containing nitrato (—ONO$_2$) and nitrito (—ONO) substituents or a product B containing nitrato and N-nitroso (>NNO) substituents, and afford, when the nitrogen oxide is N$_2$O$_5$, a product C containing nitrato substituents or a product D containing nitrato and N-nitro (>NNO$_2$) substituents;
   (b) when the nitrogen oxide is N$_2$O$_4$, oxidising with ozone product A to product C or product B to product D; and
   (c) isolating product C or product D.

2. A process for the production of a high energy polymer comprising the following steps:
   (a) reacting, in an inert organic solvent, a polyepoxide with a nitrogen oxide selected from the group consisting of dinitrogen tetroxide (N$_2$O$_4$) and dinitrogen pentoxide (N$_2$O$_5$) to afford, when the nitrogen oxide is N$_2$O$_4$, a first polymeric product containing nitrato (—ONO$_2$) and nitrito (—ONO) substituents and, when the nitrogen oxide is N$_2$O$_5$, a second polymeric product containing nitrato substituents;
   (b) when the nitrogen oxide is N$_2$O$_4$, oxidising the first polymeric product to the second polymeric product with ozone; and
   (c) isolating the second polymeric product.

3. A process according to claim 2 wherein the polyepoxide is an ipoxidised ethylenically-unsaturated polymer.

4. A process according to claim 3 wherein the polyepoxide is a 2% to 50% epoxidised polydiene.

5. A process according to claim 2 wherein the nitrogen oxide is dinitrogen pentoxide.

6. A process according to claim 1 wherein at least one of the carbon atoms on the heterocyclic nucleus of the strained ring compound is substituted by at least one radical selected from the group consisting of halo, nitro, cyano, hydroxy, azido, primary amino, a monovalent organic radical, and a divalent organic radical provided that when the at least one radical is a divalent organic radical the said radical either monosubstitutes two adjacent carbon atoms or disubstitutes the same carbon atom on the heterocyclic nucleus of the strained ring compound.

7. A process according to claim 6 wherein the organic radical is selected from the group consisting of an optionally-substituted aromatic radical, an optionally-substituted aliphatic radical, and an optionally-substituted alicyclic radical.

8. A process according to claim 7 wherein the heterocyclic strained ring compound is selected from the group consisting of propyleneimine, propylene oxide, n-but-1-ene oxide, n-but-2-ene oxide, n-pent-2-ene oxide, n-hex-1-ene oxide, n-hex-2-ene oxide, n-hex-3-ene oxide, styrene oxide, stilbene oxide, epichlorohydrin, butadiene monoepoxide, 3,3-dimethyloxetane, 3,3-(pentamethylene)-oxetane, 2-propyl-3-ethyloxetane, 3-hydroxyoxethane, spirocyclic bioxetane and butadiene diepoxide.

9. A process according to claim 1 wherein the heterocyclic strained ring compound is selected from the group consisting of N-substituted aziridines and N-substituted azetidines.

10. A process according to claim 9 wherein the N-substituent radical on the N-substituted strained ring compound is selected from the group consisting of halo, nitro, cyano, and a monovalent organic radical.

11. A process according to claim 10 wherein the organic radical is selected from the group consisting of an optionally-substituted aromatic radical, an optionally-substituted aliphatic radical, and an optionally-substituted alicyclic radical.

12. A process according to claim 11 wherein the heterocyclic strained ring compound is selected from the group consisting of 2-aziridineethanol, N-(2-cyanoethyl)-2-methylaziridine, N-(2-cyanoethyl)-aziridine, N-(n-butyl)-aziridine, N-picrylaziridine, ethyl-N,N-ethylenecarbamate, N-propyl-N,N'-propyleneurea, N-nitro-N',N'-propyleneguanidine, and N-(2-cyanoethyl)-azetidine.

13. A process according to claim 7 wherein the heterocyclic strained ring compound comprises an optionally-substituted epoxidised cyclene, which has a chemical structure corresponding to a cyclene contain 2 m ring carbon atoms and from 1 to m carbon-carbon double bonds on the cyclene ring wherein m is from 2 to 6 in which each of from 1 to m of the ethylenically-unsaturated groups of the cyclene is replaced by an epoxy group.

14. A process according to claim 13 wherein the epoxidised cyclene is selected from the group consisting of 1,2-epoxycyclohexane, 1,2,3,4,5,6-triepoxycyclohexane, and 1,2,5,6-diepoxycyclooctane.

15. A process according to claim 6 wherein the heterocyclic strained ring compound is selected from the group consisting of oxiranes and oxetanes substituted by one or more radicals, wherein at least one of the radicals comprises a organic radical substituted by at least one monovalent hydroxy group capable of conversion to a nitrate ester group when reacted with an appropriate nitrating agent.

16. A process according to claim 15 wherein at least (a$^1$+a$^2$) moles of the nitrogen oxide are reacted per mole of the heterocyclic strained ring compound, wherein a$^1$ represents the total number strained ring nuclei, selected from the nuclei of oxirane and oxetane, per molecule of strained ring compound and a$^2$ represents the total number of hydroxy groups per molecule of heterocyclic compound.

17. A process according to claim 15 wherein the hydroxy-substituted organic radical comprises a hydroxy-substituted C$_1$–C$_5$ alkyl radical.

18. A process according to claim 17 wherein the heterocyclic strained ring compound is selected from glycidol and 3-methyl-3-(hydroxymethyl) oxetane.

19. A process according to claim 4 wherein the epoxidised ethylenically-unsaturated polymer comprises a 2% to 50% epoxidised hydroxy-terminated polybutadiene.

20. A process according to claim 9 wherein the heterocyclic strained ring compound contains at least two radicals selected from the group consisting of optionally-substituted N-aziridinyl and optionally-substituted N-azetidinyl.

21. A process according to claim 20 wherein the heterocyclic strained ring compound is selected from the group consisting of diethyleneoxamide, dipropyleneurea, and N-phenyl-N′,N″-diethyleneguanidine.

22. A process according to claim 21 wherein the heterocyclic strained ring compound comprises a poly-substituted aromatic compound wherein at least two fo the substituent radicals on the aromatic nucleus are strained ring heterocyclic radicals independently selected from the group consisting of optionally-substituted oxiranyl, optionally-substituted oxetanyl, optionally-substituted aziridinyl and optionally-substituted azetidinyl radicals.

23. A process according to claim 22 wherein the poly-substituted aromatic compound is selected from the group consisting of a compound of general formula I and a compound of general formula II

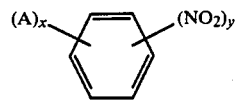

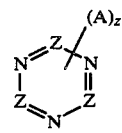

wherein
A is as defined in claim 18;
x is an integer from 2 to 4;
y is O or an integer from 1 to (6-x);
Z is an atom of valency $n^1$;
$n^1$ is 4 or 5; and
z is an integer from 2 to $3(n^1-3)$.

24. A process according to claim 23 wherein the poly-substituted aromatic compound is selected from the group consisting of N,N,N′,N′,N″,N″-triethylenemelamine, N,N,N′,N′, N″,N″-tripropylenemelamine, 2,4,6-tris-(1-azetidinyl)-1,3,5-triazine, and 2,2,4,4,6,6,-hexakis-(1′-aziridinyl)cyclotriphosphaza-1,3,5-triene.

25. A process according to claim 1 wherein the reaction, between the heterocyclic strained ring compound and the nitrogen oxide, is performed in an inert organic solvent, said inert organic solvent being a halogenated alkane selected from the group consisting of dichloromethane, chloroform, carbon tetrachloride, and a chlorofluorocarbon.

* * * * *